US009682711B2

(12) United States Patent
Lee

(10) Patent No.: US 9,682,711 B2
(45) Date of Patent: Jun. 20, 2017

(54) APPARATUS AND METHOD FOR DETECTING DRIVER STATUS

(71) Applicant: HYUNDAI MOBIS CO., LTD., Seoul (KR)

(72) Inventor: Sang-Gwon Lee, Incheon (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 91 days.

(21) Appl. No.: 14/599,230

(22) Filed: Jan. 16, 2015

(65) Prior Publication Data

US 2016/0023666 A1    Jan. 28, 2016

(30) Foreign Application Priority Data

Jul. 23, 2014   (KR) ..................... 10-2014-0093168

(51) Int. Cl.
| | |
|---|---|
| *A61B 5/024* | (2006.01) |
| *B60W 50/14* | (2012.01) |
| *B60K 28/06* | (2006.01) |
| *B60W 40/08* | (2012.01) |
| *A61B 5/00* | (2006.01) |
| *A61B 5/0205* | (2006.01) |
| *A61B 5/18* | (2006.01) |

(52) U.S. Cl.
CPC ........... *B60W 50/14* (2013.01); *A61B 5/0205* (2013.01); *A61B 5/02427* (2013.01); *A61B 5/18* (2013.01); *A61B 5/6893* (2013.01); *B60K 28/06* (2013.01); *B60W 40/08* (2013.01); *B60W 2050/143* (2013.01)

(58) Field of Classification Search
CPC ............ B60W 40/09; B60W 2540/28; B60W 2540/30; B60W 2050/143; B60T 2220/02; G08G 1/0962; G08G 1/167; G06F 17/00
USPC ......... 701/33.4, 1, 36, 45, 93; 340/438, 439, 340/500
See application file for complete search history.

(56) References Cited

U.S. PATENT DOCUMENTS

| | | | |
|---|---|---|---|
| 2005/0030184 A1* | 2/2005 | Victor .................... | B60K 28/06 340/576 |
| 2007/0182529 A1* | 8/2007 | Dobler .................. | B60K 28/06 340/438 |
| 2010/0185101 A1* | 7/2010 | Sakai ................... | A61B 5/4035 600/483 |

(Continued)

FOREIGN PATENT DOCUMENTS

| | | |
|---|---|---|
| EP | 1416349 A1 | 5/2004 |
| JP | 2002-002325 A | 1/2002 |

(Continued)

*Primary Examiner* — Dalena Tran
(74) *Attorney, Agent, or Firm* — Knobbe Martens Olson & Bear LLP

(57) ABSTRACT

An apparatus for detecting a driver status may include an information acquisition unit acquiring driver's vehicle driving information, driver's vehicle operation information, and driver status information, a calculation unit calculating a driving load indicated by converting a factor obstructing safe driving into a numerical value, based on the information acquired by the information acquisition unit, a comparison unit between the driving load calculated by the calculation unit and a preset load margin, and a warning unit warning the driver when the comparison unit determines that the calculated driving load exceeds the preset load margin.

18 Claims, 31 Drawing Sheets

(56) References Cited

U.S. PATENT DOCUMENTS

| | | | | |
|---|---|---|---|---|
| 2010/0241021 A1* | 9/2010 | Morikawa | ............... | A61B 5/048 600/544 |
| 2012/0150412 A1* | 6/2012 | Yoon | ................. | B60W 50/14 701/99 |
| 2012/0212353 A1* | 8/2012 | Fung | .................. | B60K 28/06 340/905 |
| 2013/0311043 A1* | 11/2013 | Kobana | .................. | B60J 7/22 701/41 |
| 2014/0293053 A1* | 10/2014 | Chuang | ............... | A61B 5/6893 348/148 |
| 2015/0265201 A1* | 9/2015 | Arbas | ................. | A61B 5/18 600/301 |

FOREIGN PATENT DOCUMENTS

| | | | | |
|---|---|---|---|---|
| JP | 2007-331652 | * | 12/2007 | ............... B60T 7/14 |
| JP | 4965162 B2 | | 7/2012 | |
| KR | 10-0282903 B1 | | 12/2000 | |
| KR | 10-2003-0059193 A | | 7/2003 | |
| KR | 10-2004-0094926 A | | 11/2004 | |
| KR | 10-2005-0015771 A | | 2/2005 | |
| KR | 10-2012-0066468 A | | 6/2012 | |
| KR | 10-1173944 B1 | | 8/2012 | |
| KR | 10-1311552 B1 | | 9/2013 | |
| KR | 10-2014-0022312 A | | 2/2014 | |
| WO | 2005/112764 A1 | | 12/2005 | |

\* cited by examiner

FIG.26

| Brain wave | Frequency | Characteristic |
|---|---|---|
| α | 8 ~ 12.99 Hz | RELAXATION, MEDITATION |
| β | 13 ~ 29.99 Hz | ACTIVATION, CONCENTRATION |
| γ | 30 ~ 50 Hz | SYMPATHY, EXCITEMENT |
| θ | 4 ~ 7.99 Hz | DROWSINESS |

$$P(x_i | x_j) = \frac{P(x_j | x_i) P(x_i)}{P(x_j)}$$

$$P(x_1, x_2, \cdots, x_n) = \prod_{i=1}^{n} P(x_i | \text{Parent}(x_i))$$

APPARATUS AND METHOD FOR DETECTING DRIVER STATUS

CROSS-REFERENCE TO RELATED APPLICATIONS

This application claims priority to Korean Patent Application No. 10-2014-0093168, filed on Jul. 23, 2014, which is incorporated herein by reference in its entirety.

TECHNICAL FIELD

Exemplary embodiments of the present invention relate to an apparatus and method for detecting a driver status.

BACKGROUND

In general, vehicles offer convenience of mobility and time efficiency for persons, but require care during use because of causing serious damage to surrounding persons in addition to a driver due to carelessness of the driver. Particularly, in recent years, intelligent and enhanced vehicles are gradually increased by technological convergence of vehicles and ICT (Information & Communication Technology). Thus, safe driving assistance systems provided in the vehicles serve to recognize dangerous situations and inform a driver of the recognized situations. As disclosed in Korean Patent Publication No. 10-0282903 (Dec. 2, 2000), a conventional safe driving assistance system for vehicles mainly recognizes dangerous situations by collecting information through external sensors (radar, cameras, etc.) to determine whether or not the dangerous situations (lane departures, expected collisions, etc.) are present.

SUMMARY

An embodiment of the present invention is directed to an apparatus and method for detecting a driver status, which grasp a driver's mental and physical condition to determine whether or not a driver drives a vehicle with safety and induce the driver to drive the vehicle with safety in various ways when the driver is determined not to be in a safe driving state so as to protect the driver.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an embodiment of the present invention, an apparatus for detecting a driver status includes an information acquisition unit (10) acquiring driver's vehicle driving information, driver's vehicle operation information, and driver status information, a calculation unit (20) calculating a driving load indicated by converting a factor obstructing safe driving of a driver into a quantitative numerical value, based on the information acquired by the information acquisition unit (10), a comparison unit (30) comparing between the driving load calculated by the calculation unit (20) and a preset load margin, and a warning unit (40) warning the driver when the comparison unit (30) determines that the calculated driving load exceeds the preset load margin.

The information acquisition unit (10) may include a vehicle driving information acquisition portion (11), a vehicle operation information acquisition portion (12), and a driver status information acquisition portion (13).

The vehicle driving information acquisition portion (11) may include one or more of an accelerator pedal operation sensor, a brake pedal operation sensor, a steering wheel operation sensor, a multifunctional switch operation sensor, a clutch pedal operation sensor, and a transmission operation sensor, in order to acquire information generated when the driver drives a vehicle.

The vehicle operation information acquisition portion (12) may include one or more of an air conditioning device switch operation sensor and an AVN switch operation sensor, in order to acquire information generated when the driver operates a vehicle.

The driver status information acquisition portion (13) may include one or more of a microphone, a driver observation camera, an ECG (electrocardiogram) sensor, an EEG (electroencephalogram) sensor, and a PPG (photoplethysmography) sensor, in order to acquire information according to a driver status during driving of a vehicle.

Each of the EEG sensor, the ECG sensor, and the PPG sensor may be a wearable sensor.

The calculation unit (20) may include a vehicle driving load calculation portion (21), a vehicle operation load calculation portion (22), and a driver status load calculation portion (23).

The comparison unit (30) may include a memory portion (50) for storing data of the preset load margin.

The warning unit (40) may include one or more of a warning sound output device (41), a driving load display device (42), and a vehicle control device (43).

In accordance with another embodiment of the present invention, a method of detecting a driver status includes performing information acquisition (S100) of acquiring driver's vehicle driving information, driver's vehicle operation information, and driver status information, calculating a driving load (S200) indicated by converting a load of a driver into a quantitative numerical value, based on the information acquired in the performing information acquisition (S100), comparing (S300) between the driving load of the driver calculated in the calculating a driving load (S200) and a preset load margin, and warning the driver (S400) when the driving load of the driver exceeds the preset load margin in the comparing (S300).

The performing information acquisition (S100) may include acquiring vehicle driving information (S110), acquiring vehicle operation information (S120), and acquiring driver status information (S130).

The acquiring vehicle driving information (S110) may include one or more of acquiring accelerator pedal operation information (S111), acquiring brake pedal operation information (S112), acquiring steering wheel operation information (S113), and acquiring multifunctional switch operation information (S114), in order to acquire information generated when the driver drives a vehicle.

In a manual transmission vehicle, the acquiring vehicle driving information (S110) may include one or more of acquiring clutch pedal operation information (S115) and acquiring transmission operation information (S116).

The acquiring vehicle operation information (S120) may include one or more of acquiring AVN operation information (S121) and acquiring air conditioning device operation information (S122), in order to acquire information generated when the driver operates a vehicle.

The acquiring driver status information (S130) may include one or more of acquiring driver's voice information (S131), acquiring driver's forward observation information (S132), acquiring driver's eye-closed information (S133), acquiring driver's brainwave information (S134), acquiring driver's ECG information (S135), and acquiring driver's PPG signal information (S136), in order to acquire information according to a driver status during driving of a vehicle.

The calculating a driving load (S200) may include calculating a vehicle driving load (S210), calculating a vehicle operation load (S220), calculating a driver status load (S230), and calculating a driving load by summing the respective calculated loads (S240).

The calculating a vehicle driving load (S210) may include calculating an accelerator pedal operation load (S211), calculating a brake pedal operation load (S212), calculating a multifunctional switch operation load (S213), calculating a steering wheel operation load (S214), and summing the respective calculated operation loads (S217).

In a manual transmission vehicle, calculating a vehicle driving load (S210) may include one or more of calculating a clutch pedal operation load (S215) and calculating a transmission operation load (S216).

The calculating an accelerator pedal operation load (S211) may be performed by multiplying the number of times of operation of an accelerator pedal for a preset time with a preset accelerator pedal operation load weighting.

The calculating a brake pedal operation load (S212) may be performed by multiplying the number of times of operation of a brake pedal for a preset time with a preset brake pedal operation load weighting.

The calculating a multifunctional switch operation load (S213) may be performed by multiplying the number of times of operation of a multifunctional switch for a preset time with a preset multifunctional switch operation load weighting.

The calculating a steering wheel operation load (S214) may be performed by multiplying the number of times of operation of a steering wheel for a preset time with a preset steering wheel operation load weighting.

The calculating a clutch pedal operation load (S215) may be performed by multiplying the number of times of operation of a clutch pedal for a preset time with a preset clutch pedal operation load weighting.

The calculating a transmission operation load (S216) may be performed by multiplying the number of times of operation of a transmission for a preset time with a preset transmission operation load weighting.

The calculating a vehicle operation load (S220) may include calculating a load according to operation of an AVN (S221), calculating a load according to operation of an air conditioning device (S222), and summing the respective calculated operation loads (S223).

The calculating a load according to operation of an AVN (S221) may be performed by multiplying the number of times of operation of the AVN and operation time of the AVN for a preset time with a preset AVN operation load weighting.

The calculating a load according to operation of an air conditioning device (S222) may be performed by multiplying the number of times of operation of the air conditioning device and operation time of the air conditioning device for a preset time with a preset air conditioning device operation load weighting.

The calculating a driver status load (S230) may include calculating a voice load (S231), calculating a drowsiness load (S232), calculating an observation neglect load (S233), and summing the respective calculated loads (S234).

The calculating a voice load (S231) may be performed by multiplying a received time of data of a voice having a reference value or more for a preset time with a preset voice load weighting.

The calculating a drowsiness load (S232) may be performed by multiplying a value multiplying the number of times being eye-closed and an eye-closed time for a preset time, with a preset drowsiness load weighting.

When a sum of angles of a driver's eyelid is equal to or less than a preset reference value, it may be determined that the driver closes eyes.

The calculating an observation neglect load (S233) may be performed by multiplying a time for which a driver's viewing is deviated from a visible range during no-load driving for a preset time with a preset observation neglect load weighting.

The visible range during no-load driving may be determined according to an angle of the wheel on the basis of the front of the vehicle.

Whether or not the driver's viewing is deviated from the visible range during no-load driving may be determined by measuring face angles of the driver and pupil positions of the driver.

When the driving load is equal to or greater than a first load margin and less than a second load margin, the warning the driver (S400) may perform a first warning process (S410) including one or more of generating a warning sound (S411) through a speaker, displaying a warning (S412) through an AVN or a HUD, and notifying of vibration (S413) through vibration of a steering wheel or a seat.

When the driving load is equal to or greater than a second load margin and less than a third load margin, the warning the driver (S400) may perform a second warning process (S420) of holding a function of an AVN.

When the driving load is equal to or greater than a third load margin, the warning the driver (S400) may perform a third warning process (S430) of forcibly stopping a vehicle.

The method may include performing driver status determination utilizing an ECG (electrocardiogram) (S500) of determining a driver status from the driver's ECG information and the driver's PPG (photoplethysmography) signal information after the performing information acquisition (S100).

The performing driver status determination utilizing an ECG (S500) may include detecting an HRV (Heart Rate Variability) signal (S510) from the driver's ECG information and the driver's PPG signal information.

The performing driver status determination utilizing an ECG (S500) may include deriving a heart distribution chart and a heart histogram (S520) from the result detected from the detecting of an HRV signal (S510).

The performing driver status determination utilizing an ECG (S500) may include performing driver status determination (S530) of determining whether or not the driver is in an abnormal condition from the result of the deriving of a heart distribution chart and a heart histogram (S520).

The performing driver status determination utilizing an ECG (S500) may include performing emergency control (S540) of controlling the vehicle when it is determined that the driver is in the abnormal condition in the performing driver status determination (S530).

The performing emergency control (S540) may include one or more of opening a window (S541), generating an anion (S542), playing music (S543), warning a driver (S544) through an AVN or a HUD, and safely stopping a vehicle (S545).

The method may include performing driver status determination utilizing an EEG (electroencephalogram) (S600) of determining a driver status from the driver's brainwave information after the performing information acquisition (S100).

The performing driver status determination utilizing an EEG (electroencephalogram) (S600) may include performing brainwave separation (S610) of separating respective waveforms from the driver's brainwave information for each frequency.

The performing driver status determination utilizing an EEG (S600) may include deducing a driver's status (S620) through a Bayesian network, based on the respective waveforms separated for each frequency in the performing brainwave separation (S610).

When the driver is deduced to be in a first drowsy state in the deducing a driver's status (S620), the performing driver status determination utilizing an EEG (S600) may perform a first drowsiness warning process (S630) including one or more of playing music or generating a warning sound (S621) through a speaker, displaying a warning (S622) through an AVN or a HUD, and notifying of vibration (S623) through vibration of a steering wheel or a seat.

When the driver is deduced to be in a drowsy state other than the first drowsy state in the deducing a driver's status (S620), the performing driver status determination utilizing an EEG (S600) may perform a second drowsiness warning process (S640) of safely stopping the vehicle.

When the driver is deduced to be in an anxious state in the deducing a driver's status (S620), the performing driver status determination utilizing an EEG (S600) may include providing a driving guide (S650) through the AVN or the HUD.

When the driver is deduced to be in a stable state in the deducing a driver's status (S620), the performing driver status determination utilizing an EEG (S600) may sum a brainwave load by the following equation when the driving load is calculated in the calculating of a driving load (S200):

$$W_{EED} = \varphi \times \frac{\alpha \text{ wave}}{\beta \text{ wave}}$$

$W_{EED}$=brainwave load
$\varphi$=preset brainwave load weighting
α wave=mean frequency of α wave extracted for unit time
β wave=mean frequency of β wave extracted for unit time.

When the driver is deduced to be in a concentrated state in the deducing a driver's status (S620), the performing driver status determination utilizing an EEG (S600) may not add a brainwave load to the driving load in the calculating a driving load (S200).

BRIEF DESCRIPTION OF THE DRAWINGS

FIG. 26 is a table illustrating a frequency range and characteristic of each brainwave.

DETAILED DESCRIPTION

Figure 1:
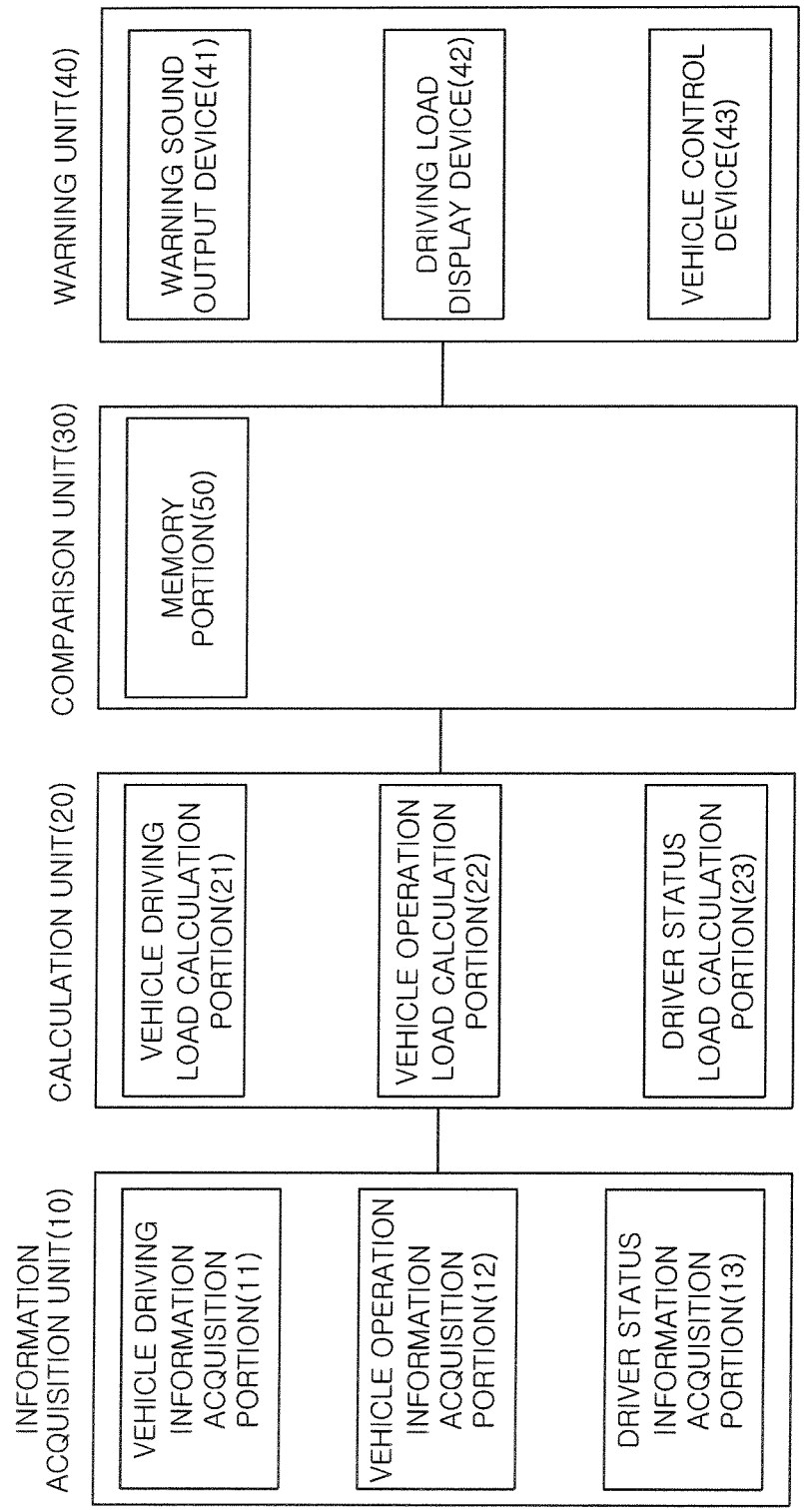
FIG. 1 is a block diagram illustrating a configuration of an apparatus for detecting a driver status according to an embodiment of the present invention.

The terms and words used in the specification and claims should not be construed as their ordinary or dictionary sense.

On the basis of the principle that the inventor can define the appropriate concept of a term in order to describe his/her own invention in the best way, it should be construed as meaning and concepts for complying with the technical idea of the present invention. Accordingly, the embodiments described in the present specification and the construction shown in the drawings are nothing but one preferred embodiment of the present invention, and it does not cover all the technical ideas of the invention. Thus, it should be understood that various changes and modifications may be made at the time of filing the present application. In addition, detailed descriptions of functions and constructions well known in the art may be omitted to avoid unnecessarily obscuring the gist of the present invention. Exemplary embodiments of the present invention will be described below in more detail with reference to the accompanying drawings.

A method of informing a driver of dangerous situations includes a method of displaying the dangerous situations on a display device (for instance, flickering of a warning lamp) or notifying of the dangerous situations by voice. However, in a system for warning a driver by flickering of the display device, voice notification, or the like, it is possible that the voice notification is inaudible due to noise during high speed driving or it is difficult to audio-visually recognize the flickering or voice notification when the driver concentrates on driving while keeping eyes forward or falls asleep at the wheel. In addition, it is also important to grasp a driver's mental and physical condition for safe driving, such as a driver's seizure or abnormal emotion status, labored respiration, neglect of observation, drowsiness, and anxiety, in regard to the driver's mental and physical condition.

Figure 2:
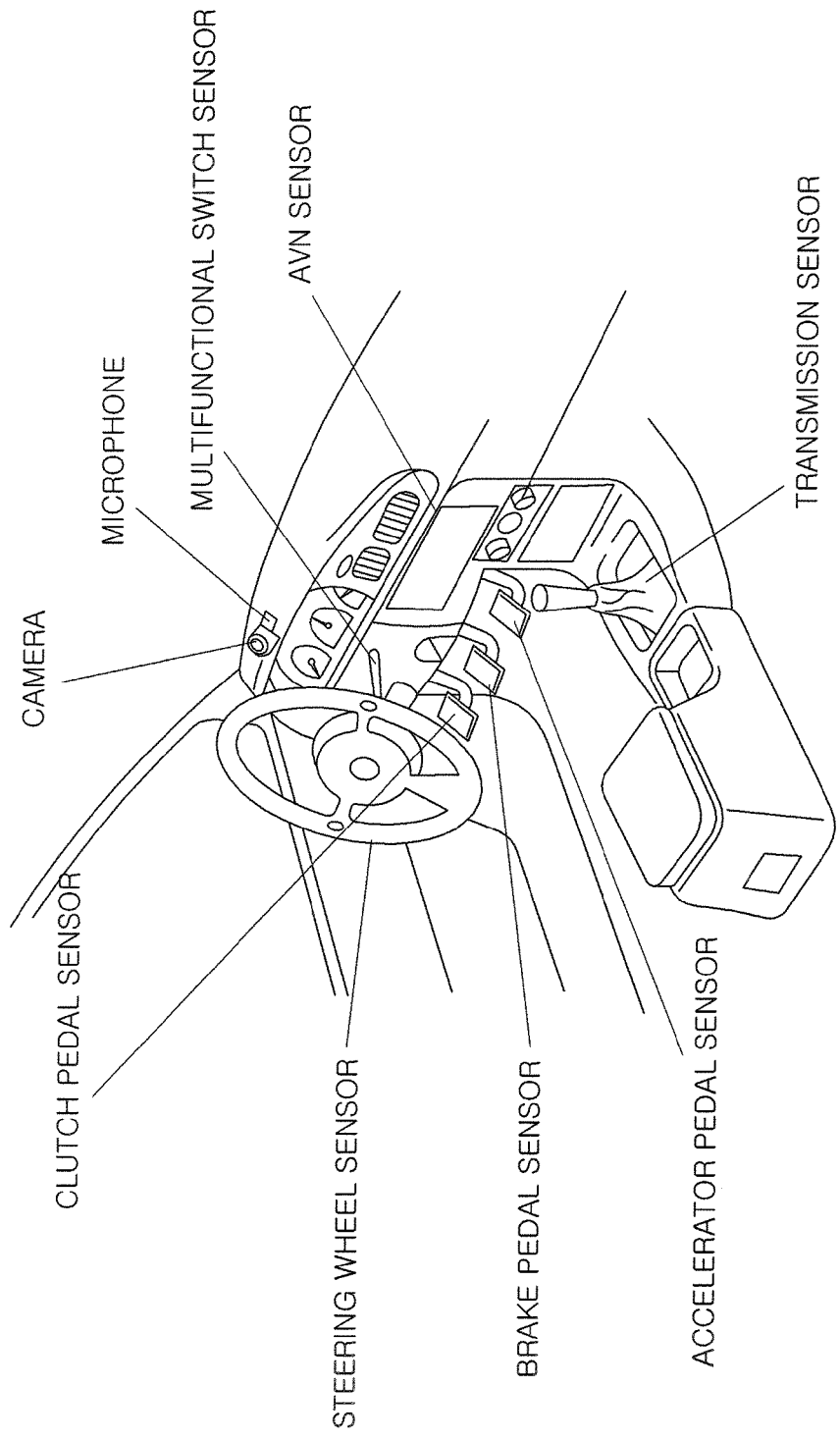
FIG. 2 is a view schematically illustrating a configuration of an information acquisition unit according to the embodiment of the present invention.
Figure 3:
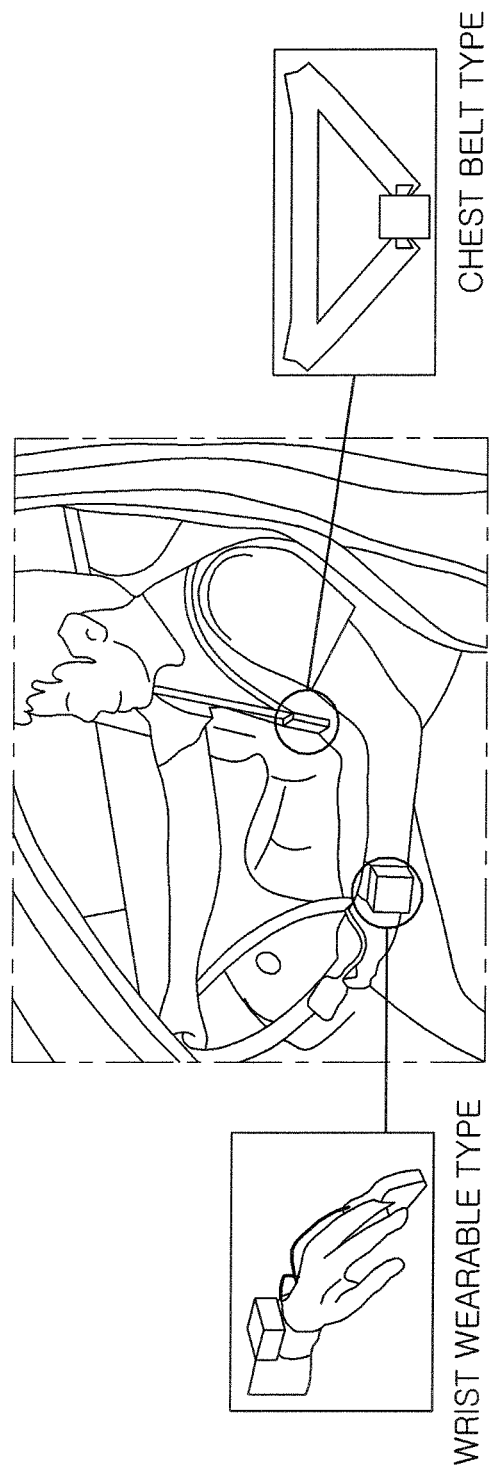
FIG. 3 is an exemplified view illustrating an ECG sensor and a PPG sensor according to the embodiment of the present invention.
Figure 4:
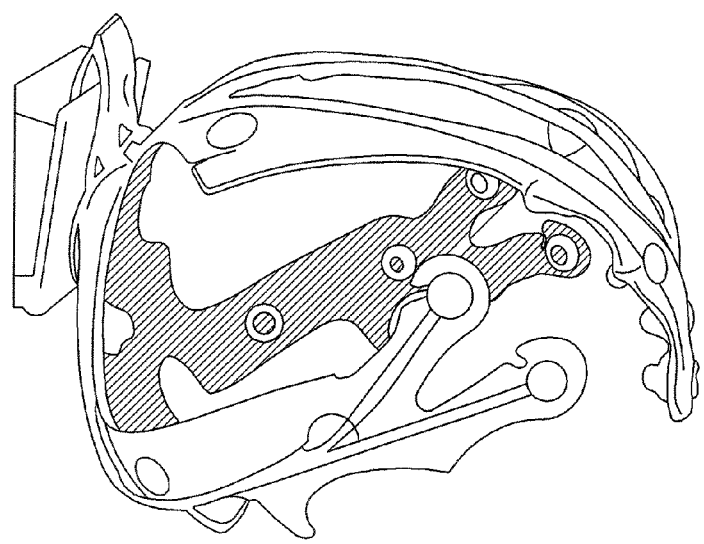
FIG. 4 is an exemplified view illustrating an EEG sensor according to the embodiment of the present invention.
Figure 5:
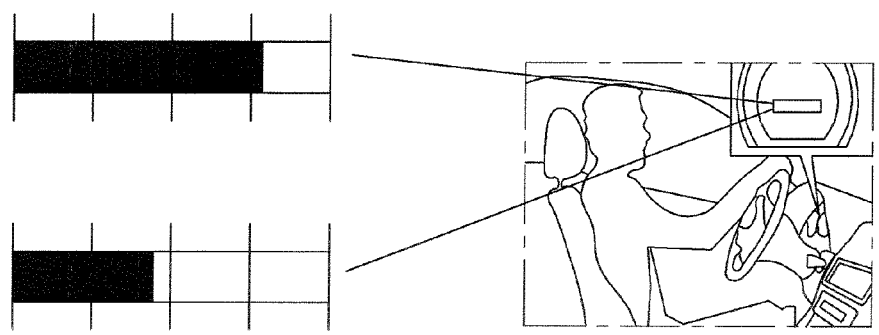
FIG. 5 is an exemplified view illustrating a driving load display device according to the embodiment of the present invention.

FIG. 1 is a block diagram illustrating a configuration of an apparatus for detecting a driver status according to an embodiment of the present invention. FIG. 2 is a view schematically illustrating a configuration of an information acquisition unit. FIG. 3 is an exemplified view illustrating an ECG sensor and a PPG sensor. FIG. 4 is an exemplified view illustrating an EEG sensor. FIG. 5 is an exemplified view illustrating a driving load display device according to the embodiment of the present invention. Referring to FIGS. 1 to 5, an apparatus for detecting a driver status according to an embodiment of the present invention includes an information acquisition unit 10 which acquires driver status information, vehicle driving information, and driver's vehicle operation information, a calculation unit 20 which calculates a driving load of a driver based on the information acquired by the information acquisition unit 10, a comparison unit 30 which comparing between the driving load calculated by the calculation unit 20 and a preset load margin, and a warning unit 40 which warns the driver when the comparison unit 30 determines that the driving load exceeds the preset load margin. The information acquisition unit 10 is a component to acquire the vehicle driving information, the vehicle operation information, and the driver status information.

The vehicle driving information is information generated when the driver drives a vehicle, and means, for example, information such as how often the driver steps on an accelerator pedal, how often the driver steps on a brake pedal, how often the driver operates a steering wheel, and how often the driver operates a multifunctional switch. In addition, in a manual transmission vehicle, the driving information may include information such as how often the driver steps on a clutch pedal and how often the driver operates a transmission, besides the above information. The multifunctional switch means a switch of a wiper, a turn signal indicator, a lighting lamp, or the like. Since the multifunctional switch is a factor necessary to the vehicle driving, operation information of the multifunctional switch may be included in the vehicle driving information. The vehicle operation information is information generated when the driver operates the vehicle, and may include, for example, information such as how often the driver operates an AVN (Audio Video Navigation) and how often the driver operates an air conditioning device. The driver status information is information according to a driver status during driving, and may include, for example, information such as how long the driver makes conversation (including a telephone conversation), whether or not the driver drowses, whether or not the driver keeps eyes forward, and whether or not abnormality is generated in a driver's electrocardiogram or brainwave.

To acquire the above information, the information acquisition unit 10 may include a vehicle driving information acquisition portion 11, a vehicle operation information acquisition portion 12, and a driver status information acquisition portion 13. The vehicle driving information acquisition portion 11 may include an accelerator pedal sensor, a brake pedal sensor, a steering wheel sensor, a multifunctional switch sensor, a clutch pedal sensor, a transmission sensor. The vehicle operation information acquisition portion 12 may include an air conditioning device sensor and an AVN sensor. The driver status information acquisition portion 13 may include a microphone, a driver observation camera, an ECG (electrocardiogram) sensor, an EEG (electroencephalogram) sensor, and a PPG (photoplethysmography) sensor.

The microphone is a component to recognize whether or not the driver makes conversation (including a telephone conversation) and the driver observation camera is a component to recognize whether or not the driver drowses or keeps eye forward by capturing a driver's face image or eye area image. The ECG sensor is a component to recognize a driver's electrocardiogram and the PPG sensor is a component to recognize a driver's PPG signal. The PPG signal may mean a photoplethysmography. The ECG sensor and the PPG sensor may be a wearable sensor, and, particularly, may have a wearable structure such as a chest belt type or a wristwatch type. The ECG sensor and the PPG sensor may be worn on a driver's body to accurately measure an electrocardiogram and a photoplethysmography. The EEG sensor is to acquire driver's brainwave information and may be a wearable sensor. Particularly, the EEG sensor may have a wearable structure such as a headset type. The EEG sensor may be worn on a driver's body to accurately measure a brainwave.

The calculation unit 20 calculates a driving load indicated by converting each factor having a negative effect on safe driving of the driver into a quantitative numerical value, based on the information acquired by the information acquisition unit 10. The calculation unit 20 may include a vehicle driving load calculation portion 21, a vehicle operation load calculation portion 22, and a driver status load calculation portion 23. The driving load may be calculated by summing loads calculated by the respective calculation portions 21, 22, and 23.

The comparison unit 30 comparing between the driving load calculated by the calculation unit 20 and a preset load margin. When the driving load is equal to or less than the preset load margin, the comparison unit 30 determines that the driver is in a safe driving state. On the other hand, when the driving load exceeds the preset load margin, the comparison unit 30 determines that the driver is not in the safe driving state. The preset load margin may be an experimental value extracted from a sum of a vehicle driving load, a vehicle operation load, and a driver status load through an experiment according to conditions of a test subject. In addition, the preset load margin may be a value of the driving load calculated based on information according to existing driving patterns of the driver. The comparison unit 30 may include a memory portion 50 for storing a value of the preset load margin. The memory portion 50 may be a nonvolatile memory as a storage means for storing data.

The warning unit 40 is a component to warn the driver when the comparison unit 30 determines that the driver is not in the safe driving state, and may include a warning sound output device 41, a driving load display device 42, and a vehicle control device 43. As shown in FIG. 5, the driving load display device 42 may be mounted on a dashboard of the vehicle. In addition, the driving load may also be displayed through an AVN or a HUD (Head Up Display). When the driver is determined not to be in the safe driving state, the warning sound output device 41 may generate a warning sound to the driver or play an announcement for notifying that the driver is not in the safe driving state. The warning sound output device 41 may also utilize a speaker installed to the vehicle. The vehicle control device 43 is a device to safely stop the vehicle when the driver is determined not to be in the safe driving state, and may be a device for controlling a steering wheel, a transmission, and a brake which are installed to the vehicle.

The information acquisition unit 10, the calculation unit 20, the comparison unit 30, the warning unit 40, and the memory portion 50 may also be interconnected in a wireless manner using Bluetooth, ZigBee, WiFi, etc. or in a wired manner using RS-232, RS-485, CAN, etc.

Figure 6:
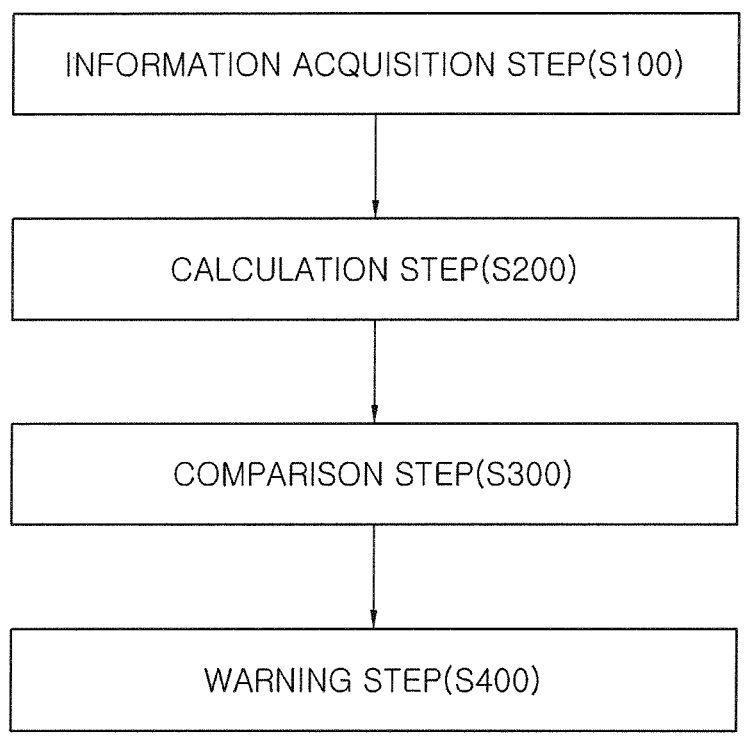
FIG. 6 is a flowchart schematically illustrating a method of detecting a driver status according to another embodiment of the present invention.
Figure 7:
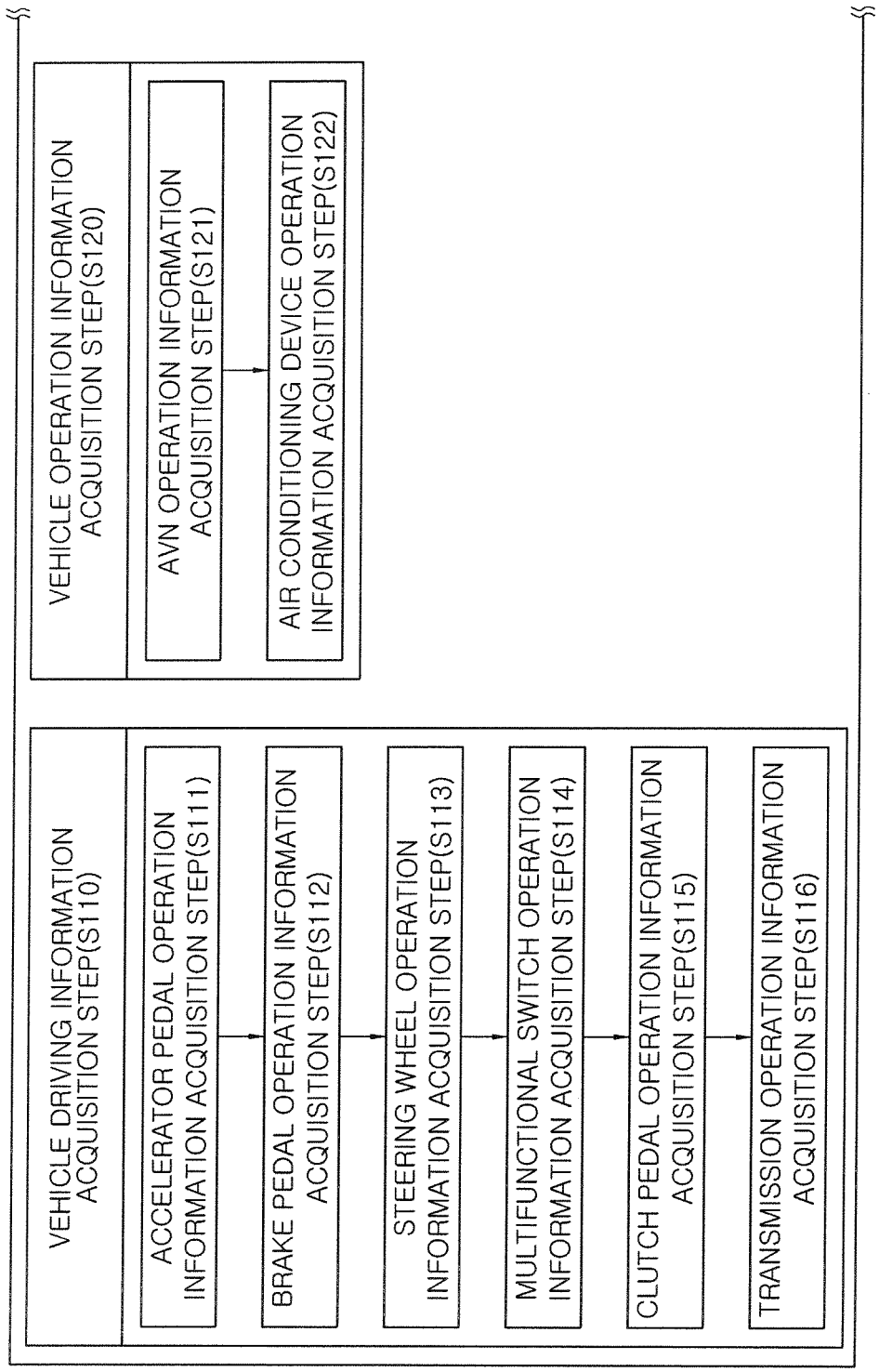
FIGS. 7 and 8 are flowcharts illustrating an information acquisition step in the method of detecting a driver status according to the embodiment of the present invention.
Figure 8:
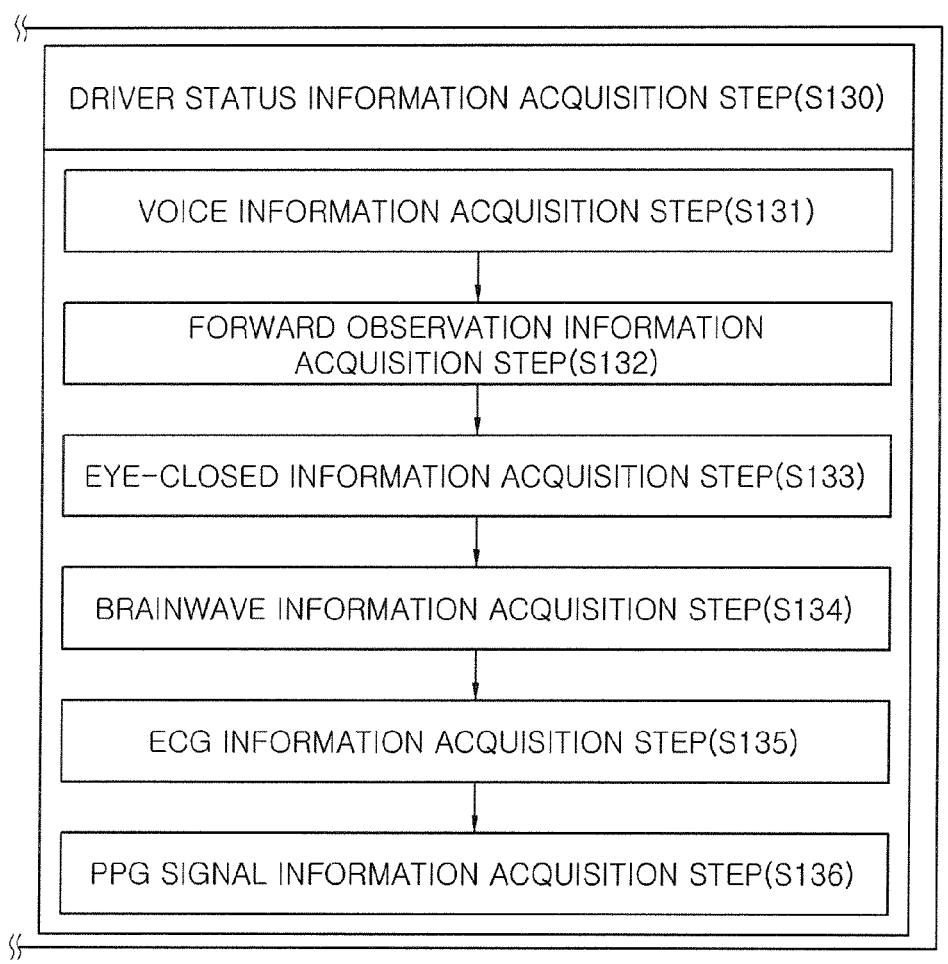
Figure 9:
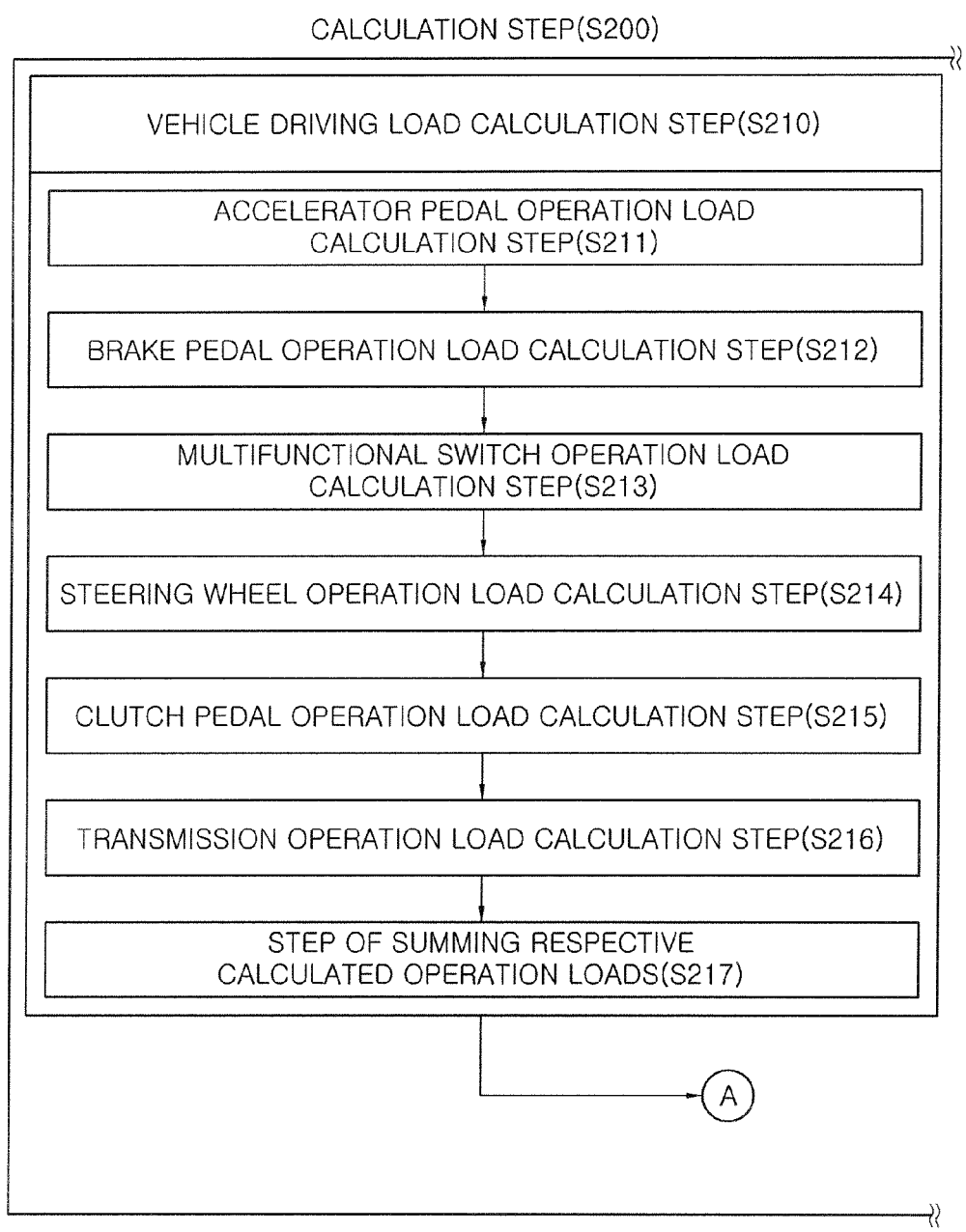
FIGS. 9 and 10 are flowcharts illustrating a calculation step in the method of detecting a driver status according to the embodiment of the present invention.
Figure 10:
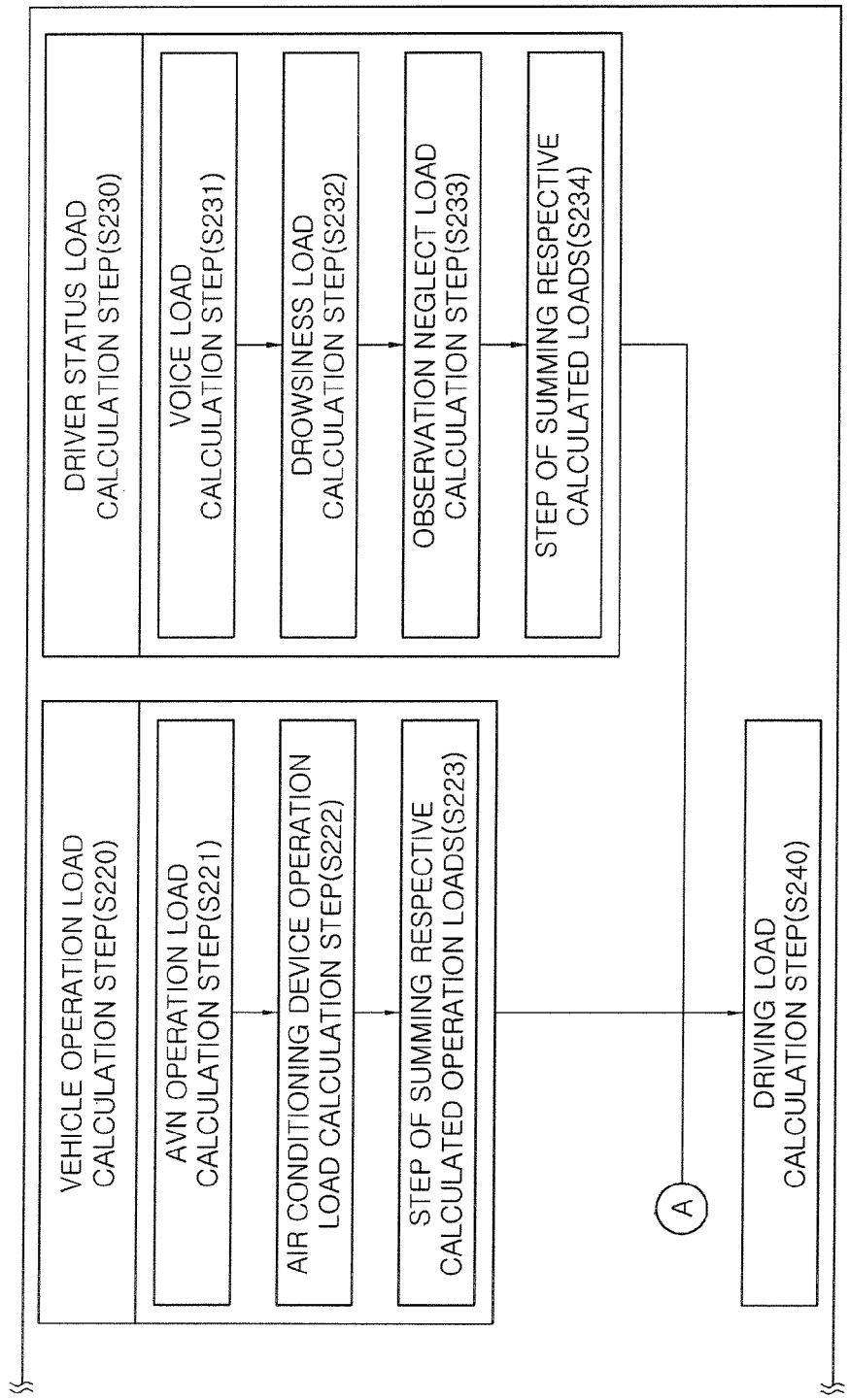
Figure 11:
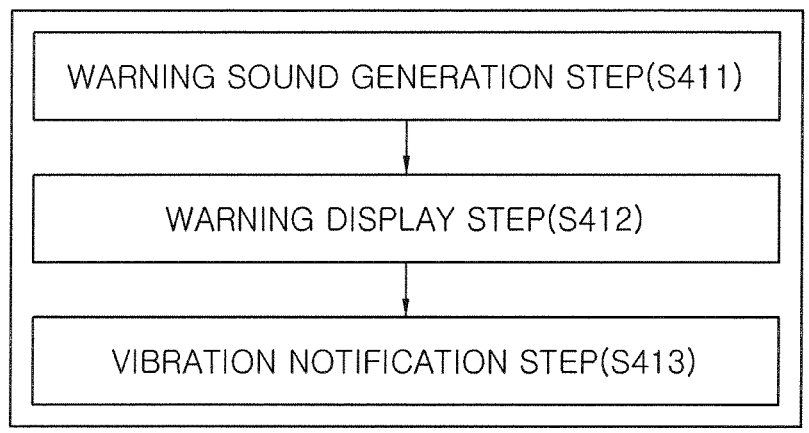
FIG. 11 is a flowchart illustrating a first warning step in the method of detecting a driver status according to the embodiment of the present invention.
Figure 12:
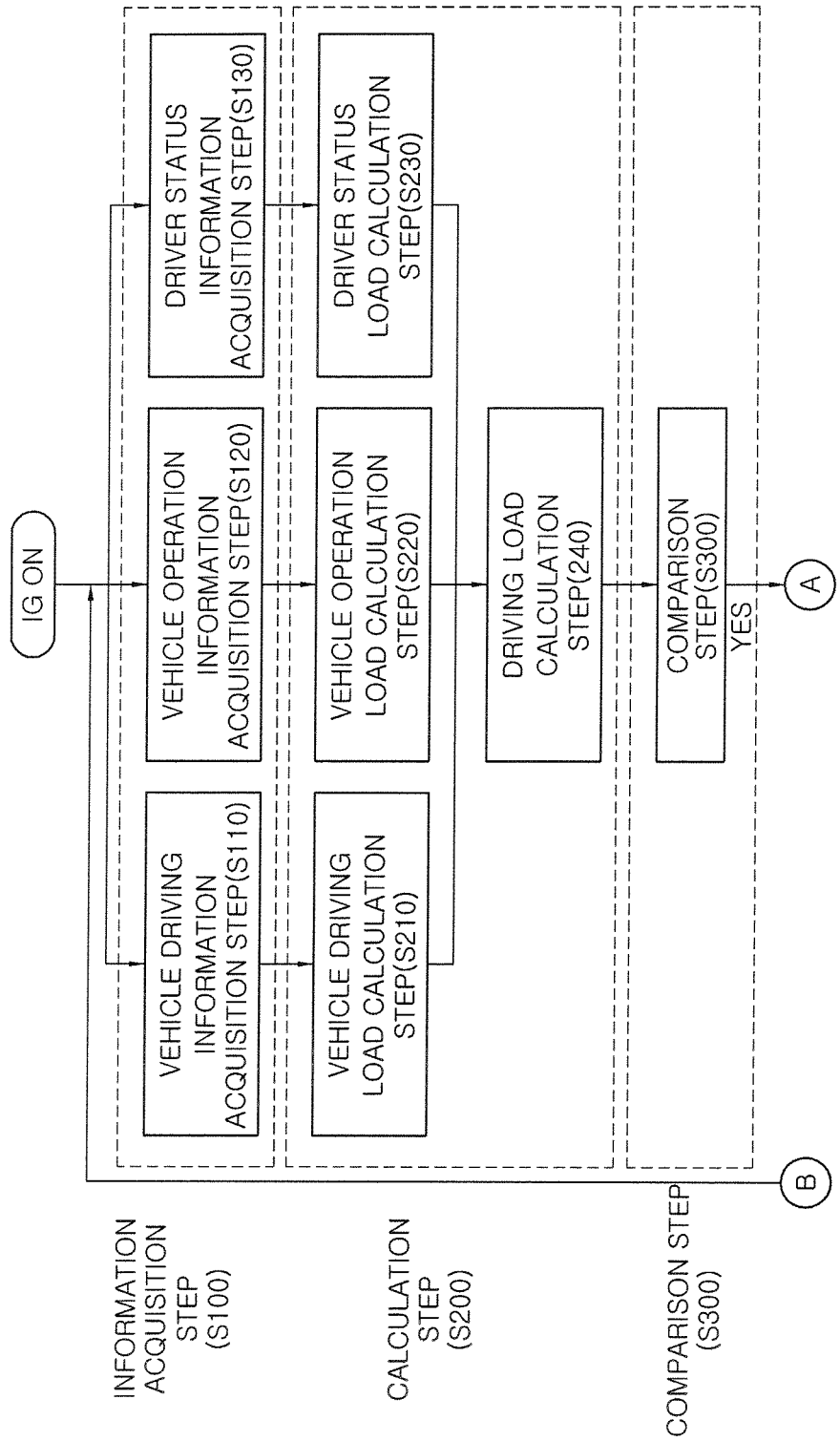
FIGS. 12 and 13 are flowcharts illustrating the method of detecting a driver status according to the embodiment of the present invention.
Figure 13:
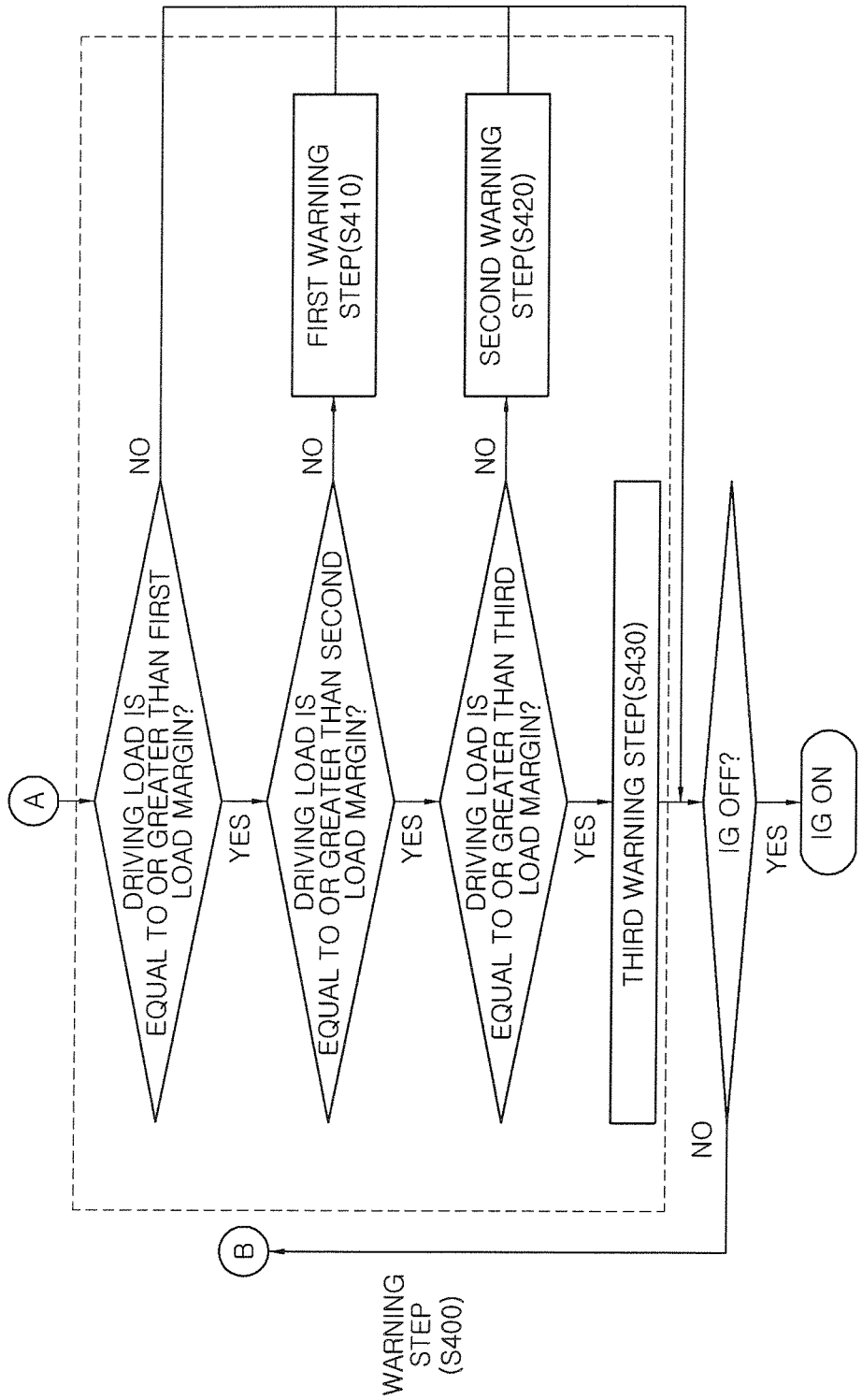
Figure 14:
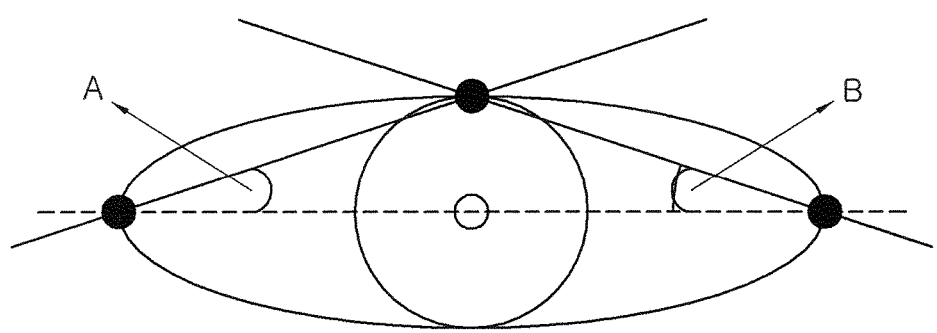
FIG. 14 is a view for explaining a method of determining that a driver closes eyes in the method of detecting a driver status according to the embodiment of the present invention.
Figure 15:
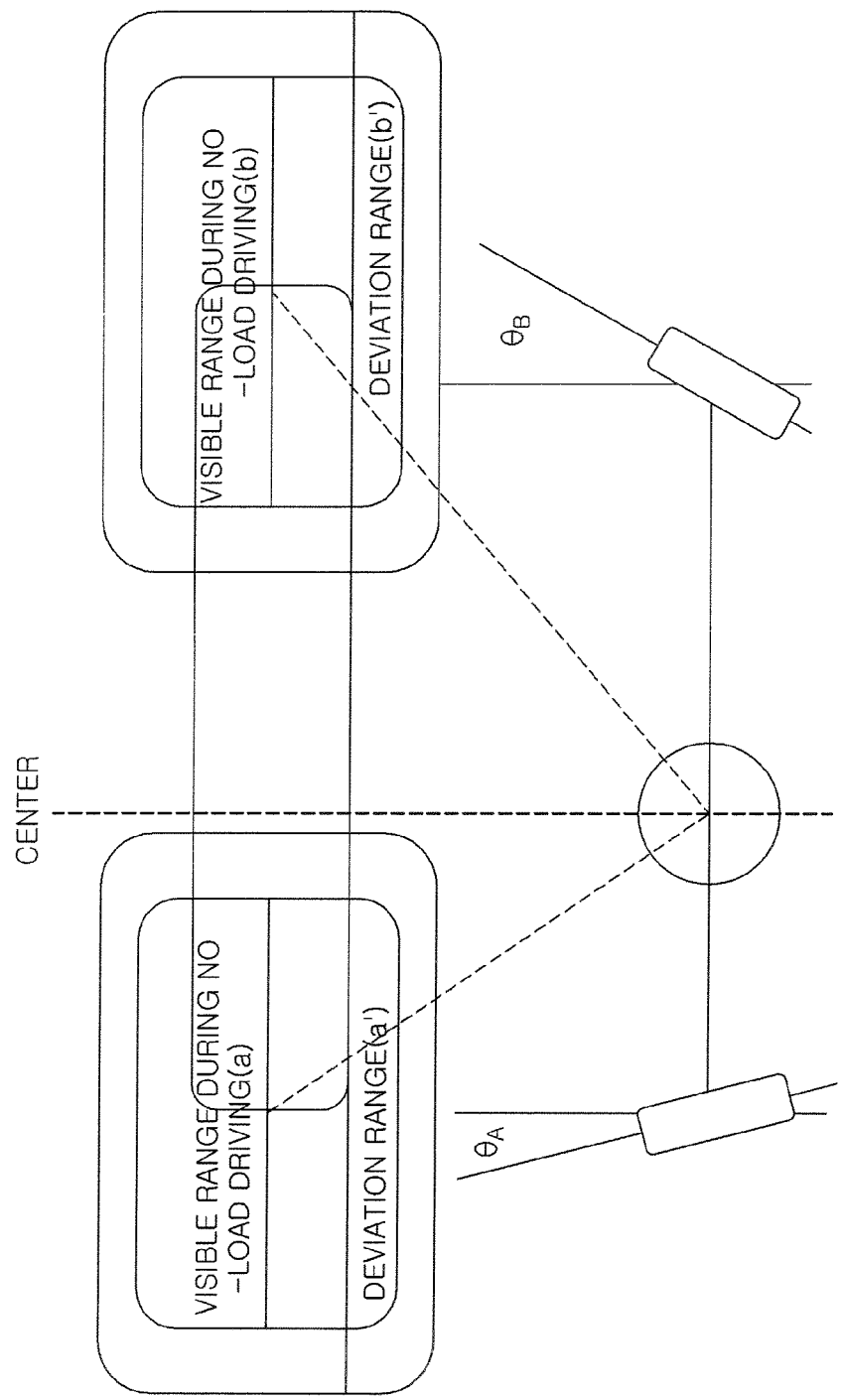
FIG. 15 is a view for explaining a visible range during no-load driving depending on a wheel angle in the method of detecting a driver status according to the embodiment of the present invention.
Figure 16:
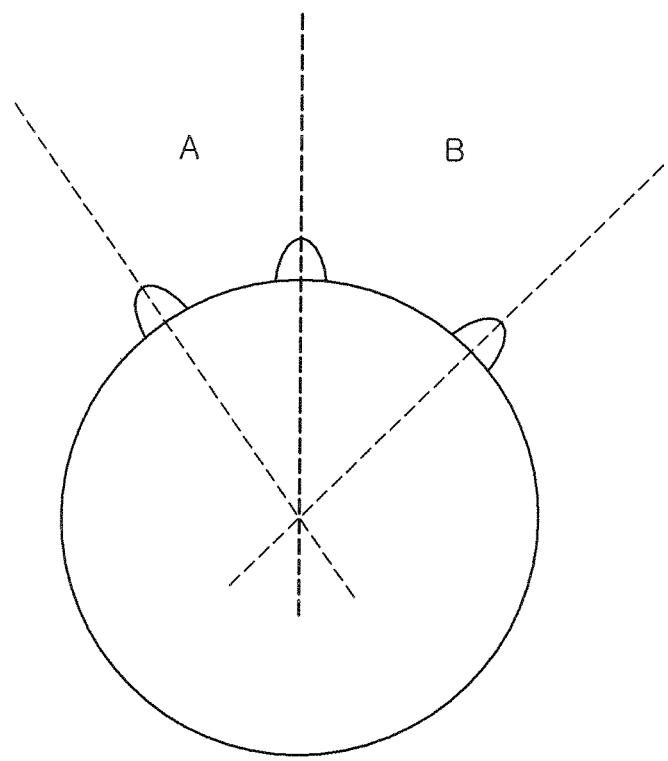
FIGS. 16 and 17 are views for explaining a method of determining a driver's viewing range in the method of detecting a driver status according to the embodiment of the present invention.
Figure 17:
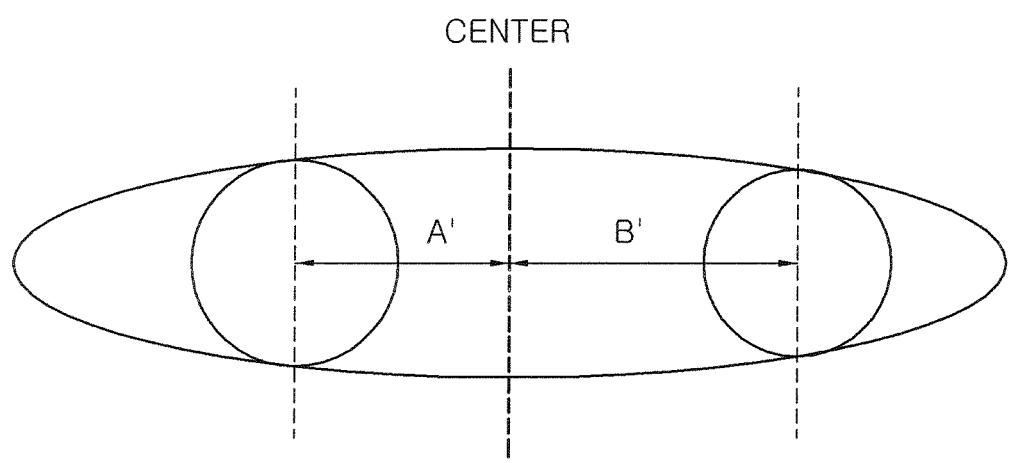

FIG. 6 is a flowchart schematically illustrating a method of detecting a driver status according to another embodiment of the present invention. FIGS. 7 and 8 are detailed flowcharts illustrating an information acquisition step. FIGS. 9 and 10 are flowcharts illustrating a calculation step. FIG. 11 is a flowchart illustrating a first warning step. FIGS. 12 and 13 are flowcharts illustrating the method of detecting a driver status. FIG. 14 is a view for explaining a method of determining that the driver closes eyes. FIG. 15 is a view for explaining a visible range during no-load driving. FIGS. 16 and 17 are views for explaining a method of determining a driver's viewing range. Referring to FIGS. 6 to 17, a method of detecting a driver status according to another embodiment of the present invention includes an information acquisition step S100 which acquires driver status information and driver's vehicle operation information, a calculation step S200 which calculates a driving load of a driver based on the information acquired in the information acquisition step S100, a comparison step S300 which compares the driving load of the driver calculated in the calculation step S200 and a preset load margin, and a warning step S400 which warns the driver when the comparison step S300 determines that the driving load of the driver exceeds the preset load margin.

In the information acquisition step S100, information of the driver is acquired by a sensor, a microphone, a camera, etc. The information acquisition step S100 includes a vehicle driving information acquisition step S110 of measuring the number of times the driver operates a pedal or the like for driving the vehicle, an operation time of the pedal or the like by the driver, etc., a vehicle operation information acquisition step S120 of measuring the number of times the driver operates a switch or the like for operating additional devices, an operation time of the switch or the like by the driver, etc., and a driver status information acquisition step S130 of measuring a conversation time of the driver, an eye-closed time of the driver, a time for which the driver does not keep eyes forward, a driver's brainwave, a driver's electrocardiogram, etc.

The vehicle driving information acquisition step S110 includes an accelerator pedal operation information acquisition step S111 of measuring the number of times the driver operates an accelerator pedal for a preset unit time, a brake pedal operation information acquisition step S112 of measuring the number of times the driver operates a brake pedal for a preset unit time, a steering wheel operation information acquisition step S113 of measuring an angle change rate of a steering wheel rotated by the driver for a preset unit time, and a multifunctional switch operation information acquisition step S114 of measuring the number of times the driver operates a multifunctional switch such as a wiper or a turn signal indicator for a preset unit time. Particularly, in a manual transmission vehicle, the vehicle driving information acquisition step S110 further includes a clutch pedal operation information acquisition step S115 of measuring the number of times the driver operates a clutch pedal for a preset unit time and a transmission operation information acquisition step S116 of measuring the number of times the driver operates a transmission for a preset unit time. The vehicle operation information acquisition step S120 includes an AVN operation information acquisition step S121 of measuring an operation time of an AVN by the driver and the number of times the driver operates the AVN, for a preset unit time, and an air conditioning device operation information acquisition step S122 of measuring an operation time of an air conditioning device such as a heater or an air conditioner by the driver and the number of times the driver operates the air conditioning device, for a preset unit time.

The driver status information acquisition step S130 includes a driver's voice information acquisition step S131 of sensing a voice of the driver through a microphone mounted at a predetermined position within the vehicle to measure a pulse amplitude (a voice amplitude) of the received voice data and a generation time of the voice having a pulse amplitude of a reference value or more, a driver's forward observation information acquisition step S132 of measuring a time for which a driver's viewing range is deviated from a visible range during no-load driving as a range, in which safe driving is not obstructed, using a driver's face image and eye area image captured by a camera mounted at a predetermined position within the vehicle, a driver's eye-closed information acquisition step S133 of measuring the number of times the driver closes eyes and an eye-closed time using a driver's eye area image captured by the camera mounted at a predetermined position within the vehicle, a driver's brainwave information acquisition step S134, a driver's ECG information acquisition step S135, and a PPG signal information acquisition step S136 of measuring a driver's photoplethysmographic signal. The respective information acquisition steps are not necessary to be sequentially performed. For example, the information acquisition steps may be simultaneously or reversely performed.

The calculation step S200 includes a vehicle driving load calculation step S210 of calculating a vehicle driving load indicated by converting each factors obstructing safe driving into a quantitative numerical value in connection with vehicle driving by the driver, a vehicle operation load calculation step S220 of calculating a vehicle operation load indicated by converting each factors obstructing safe driving into a quantitative numerical value in connection with vehicle operation by the driver, and a driver status load calculation step S230 of calculating a driver status load indicated by converting each factors obstructing safe driving into a quantitative numerical value in connection with a driver's mental and physical condition, and a driving load calculation step S240 of calculating a driving load by summing the respective calculated loads.

The vehicle driving load calculation step S210 includes an accelerator pedal operation load calculation step S211, a brake pedal operation load calculation step S212, a multifunctional switch operation load calculation step S213, a steering wheel operation load calculation step S214, and a step S217 of summing the respective calculated operation loads. Since the safe driving may be obstructed when the driver frequently operates the accelerator pedal, the brake pedal, the multifunctional switch, the steering wheel, etc., the above steps may be included in the vehicle driving load calculation step S210. The vehicle driving load calculation step S210 is performed only when a vehicle speed exceeds a preset speed. In accordance with an exemplary embodiment of the present invention, in a case in which a preset speed is 10 km/h, a vehicle driving load becomes 0 when a vehicle speed by a driver is 9 km/h. In the vehicle driving load calculation step S210, the vehicle driving load is calculated by calculating the number of times of operation or operation time of each term included in the vehicle driving information acquired in the vehicle driving information acquisition step S110 and a weighting preset at the term. The preset weighting may be set by an experiment according to each vehicle driving load. In addition, the preset weighting may be a value calculated based on information according to existing driving patterns of the driver. The preset weighting may be stored in the memory portion 50.

In accordance with another exemplary embodiment of the present invention, a vehicle driving load $W_d$ is calculated for every 200 ms. Each term is measured in 50 ms and communication is performed in a CAN manner. In a state in which a vehicle starts up, the vehicle driving load begins to be calculated when a vehicle speed is 10 km/h or more.

(1) When an IG is turned ON, a vehicle speed is 10 km/h or more, a timer 1 is set as 200 ms, and a timer 2 is set as 50 ms, whether or not an accelerator pedal is operated is measured for every 50 ms and a preset accelerator pedal operation load weighting is loaded from a memory.

(2) When the IG is turned ON, the vehicle speed is 10 km/h or more, the timer 1 is set as 200 ms, and the timer 2 is set as 50 ms, whether or not a brake pedal is operated is measured for every 50 ms and a preset brake pedal operation load weighting is loaded from the memory.

(3) When the IG is turned ON, the vehicle speed is 10 km/h or more, and the timer 1 is set as 200 ms, whether or not a multifunctional switch is operated is measured for 200 ms and a preset multifunctional switch operation load weighting is loaded from the memory.

(4) When the IG is turned ON, the vehicle speed is 10 km/h or more, the timer 1 is set as 200 ms, and the timer 2 is set as 50 ms, an angle change rate of a steering wheel is operated is measured for every 50 ms and a preset steering wheel operation load weighting is loaded from the memory.

(5) The vehicle driving load $W_d$ for 200 ms is calculated according to the following equation:

$$W_d = D_A \times n_A \times 50 \text{ ms} + D_B \times n_B \times 50 \text{ ms} + D_M \times n_M + \theta \times n_\theta \times 50 \text{ ms}$$

$W_d$=vehicle driving load
$D_A$=accelerator pedal operation load weighting
$n_A$=number of times of operation of accelerator pedal
$D_B$=brake pedal operation load weighting
$n_B$=number of times of operation of brake pedal
$D_M$=multifunctional switch operation load weighting
$n_M$=number of times of operation of multifunctional switch
$\theta$=steering wheel operation load weighting
$n_\theta$=total angle change rate of steering wheel.

(6) Each term included in the vehicle driving information and the vehicle driving load may be added or omitted, if necessary. For example, in the manual transmission vehicle, the vehicle driving load may be calculated by adding a clutch pedal operation load and a transmission operation load.

In accordance with still another exemplary embodiment of the present invention, a vehicle driving load $W_M$ may be calculated by calculating the number of times of operation of each term included in the acquired vehicle operation information and a weighting preset at the term, according to the following equation:

$$W_M = \frac{D_C \times n_C \times T_C}{T_{preset\ time}} + \frac{D_D \times n_D \times T_D}{T_{preset\ time}}$$

$W_M$=vehicle operation load
$T_{preset\ time}$=preset time
$D_C$=AVN operation load weighting
$n_C$=number of times of operation of AVN
$T_C$=AVN operation time
$D_D$=air conditioning device operation load weighting
$n_D$=number of times of operation of air conditioning device
$T_D$=air conditioning device operation time.

In accordance with yet another exemplary embodiment of the present invention, a driver status load may be calculated by calculating an operation time of each term included in the acquired driver status information and a weighting preset at the term.

A voice load V may be calculated by sensing a voice of the driver through a microphone mounted at a predetermined position within the vehicle and using a pulse amplitude (a voice amplitude) of the received voice data and information of a generation time of the voice, according to the following equation:

$$V = \frac{T_V}{T_{preset\ time}} \times D_V$$

V=voice load
$T_{preset\ time}$=preset time
$T_V$=generation time of voice having pulse amplitude of reference value or more
$D_V$=voice load weighting.

Driver's eye-closed information may be acquired using a driver's eye area image captured by a camera mounted at a predetermined position within the vehicle. The camera may have a near infrared LED to capture images at the daytime and the nighttime. Referring to FIG. 14, when a sum of $\angle A$ and $\angle B$ as angles of an eyelid is equal to or less than $\angle C$ as a preset reference value ($\angle A + \angle B \leq \angle C$) at the time of sensing an eyelid area from the eye area image, it is determined that the driver closes eyes. A drowsiness load may be calculated by identifying an angle of a driver's eyelid for every preset time to sense the number of times the driver closes eyes and calculating the number of time being eye-closed for the preset time and an eye-closed time, according to the following equation:

$$P = \frac{T_p \times n_p}{T_{preset\ time}} \times D_p$$

P=drowsiness load
$T_{preset\ time}$=preset time
$T_P$=eye-closed time
$n_P$=number of time being eye-closed
$D_P$=drowsiness load weighting.

Driver's forward observation information may be acquired using the driver's face image and eye area image captured by the camera mounted at a predetermined position within the vehicle. The camera may have a near infrared LED to capture images at the daytime and the nighttime. Referring to FIG. 15, visible ranges during no-load driving a and b are determined based on angles of the wheel. That is, the visible ranges during no-load driving a and b are determined by angle rates $\theta_A$ and $\theta_B$ changed on the basis of a central direction. Referring to FIGS. 16 and 17, a driver's viewing range is determined by face angles of the driver (see FIG. 16) and pupil positions of the driver (see FIG. 17) captured by the camera. An observation neglect load is generated when a driver's current viewing range is deviated from the visible ranges during no-load driving a and b, and a preset observation neglect load weighting may vary according to a range corresponding to the driver's current viewing range. The observation neglect load begins to be calculated when the vehicle speed is 10 km/h or more in a state in which the vehicle starts up. The observation neglect load may be calculated by the following equation:

$$E = \frac{T_E}{T_{preset\ time}} \times D_E$$

E=observation neglect load
$T_{preset\ time}$=preset time
$T_E$=time for which driver's viewing range is deviated from visible range during no-load driving
$D_E$=observation neglect load weighting.

As described above, the driver status load may be calculated at S230 by performing a voice load calculation step S231, a drowsiness load calculation step S232, and an observation neglect load calculation step S233, and then performing a step S234 of summing the respective loads, according the following equation:

$W_i = V + P + E$ $W_i$=driver status load
V=voice load
P=drowsiness load
E=observation neglect load.

In addition, as described above, the driving load may be calculated at S200 by performing the vehicle driving load calculation step S210, the vehicle operation load calculation step S220, and the driver status load calculation step S230, and then driving load calculation step S240, according the following equation:

$W_{total} = W_d + W_M + W_i$ $W_{total}$=driving load
$W_d$=vehicle driving load
$W_M$=vehicle operation load
$W_i$=driver status load.

The comparison step S300 compares between the driving load of the driver calculated in the calculation step S200 and a preset load margin. When the driving load is equal to or less than the preset load margin, it is determined that the driver is in a safe driving state. On the other hand, when the driving load exceeds the preset load margin, it is determined that the driver is not in the safe driving state. The preset load margin may be an experimental value extracted from a sum of a vehicle driving load, a vehicle operation load, and a driver status load through an experiment according to conditions of a test subject. In addition, the preset load margin may be a value of the driving load calculated based on information according to existing driving patterns of the driver. The preset load margin includes a first load margin, a second load margin, and a third load margin. The preset load margin may be stored in the memory portion 50. The memory portion 50 may be a nonvolatile memory as a storage means for storing data.

As shown in FIG. 11, the warning step S400 includes a first warning step S410, a second warning step S420, and a third warning step S430. The warning step S400 serves to guide safe driving by performing respective steps of different warning levels depending on signals transferred from the comparison step S300 to inform of a warning corresponding to the driver status. The first warning step S410 is performed when the driving load is equal to or greater than a first load margin and less than a second load margin, and includes a warning sound generation step S411 through a speaker, a warning display step S412 through an AVN or a HUD (Head Up Display), and a vibration notification step S413 through vibration of a steering wheel or a seat. The warning sound generation step S411 plays an announcement or a warning sound for notifying that the driver is not in the safe driving state through the speaker. The warning display step S412 displays a warning message or a warning icon for notifying that the driver is not in the safe driving state through the AVN or the HUD. The vibration notification step S413 induces the driver to have awareness by generating vibration to the steering wheel or the seat. The first warning step S410 is a step of the lowest warning level in the warning step S400.

The second warning step S420 is performed when the driving load is equal to or greater than a second load margin and less than a third load margin, and holds functions of the AVN. That is, since there is a high possibility of safe driving being obstructed when the AVN is operated for a long time, the second warning step S420 induces the driver to concentrate on driving of the vehicle by allowing the AVN to not operate. The second warning step S420 is a step of an intermediate warning level in the warning step S400.

The third warning step S430 is performed when the driving load is equal to or greater than a third load margin, and is a step of safely stopping the vehicle through steering wheel control, transmission control, and brake control. The third warning step S430 is a step of the highest warning level in the warning step S400. When it is determined that the driver may not safely drive the vehicle any more, the third warning step S430 is a step of stopping the vehicle in a safe region through the steering wheel control, the transmission control, and the brake control so as to safely protect the driver.

In accordance with another exemplary embodiment of the present invention, when a first warning step S410 is a first warning, the first warning step S410 may include a warning sound generation step S411 through a speaker, a warning display step S412 through an AVN or a HUD, and a notification step S413 through vibration of a steering wheel or a seat. Since the first warning step S410 is a first warning, the first warning step S410 performs a slight warning for informing the driver of an unsafe driving state. After the first warning step S410 is performed, the process is returned to the information acquisition step S100. Then, the calculation step S200 and the comparison step S300 are performed again so as to determine whether or not the driver is restored to a safe driving state. When it is determined that the driver is not restored to the safe driving state despite execution of the first warning step S410, a second warning step S420 is performed. When the second warning step S420 is a second warning, the second warning step S420 limits functions of an AVN. That is, when the driver operates the AVN despite execution of the first warning step S410, the second warning step S420 stops operation of the AVN to alert the driver to awareness. After the second warning step S420 is performed, the information acquisition step S100, the calculation step S200, and the comparison step S300 are performed again so as to determine whether or not the driver is restored to the safe driving state. When it is determined that the driver is not restored to the safe driving state despite execution of the second warning step S420, a third warning step S430 is performed. When the third warning step S430 is a third warning, the third warning step S430 safely stops the vehicle through steering wheel control, transmission control, and brake control. That is, when the driver is not restored to the safe driving state despite the first and second warnings, the vehicle is autonomously stopped in a safe region against control of the driver. Consequently, it may be possible to protect the driver which is not personally restored to the safe driving state.

Figure 18:
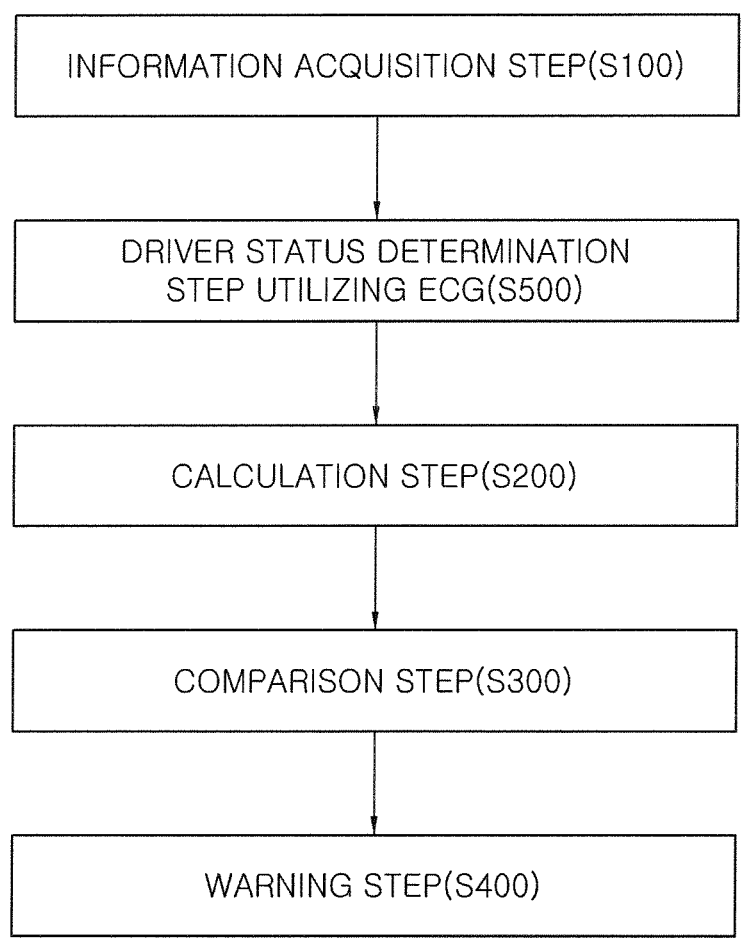
FIG. 18 is a flowchart schematically illustrating a method of detecting a driver status which includes a driver status determination step utilizing an ECG according to still another embodiment of the present invention.
Figure 19:
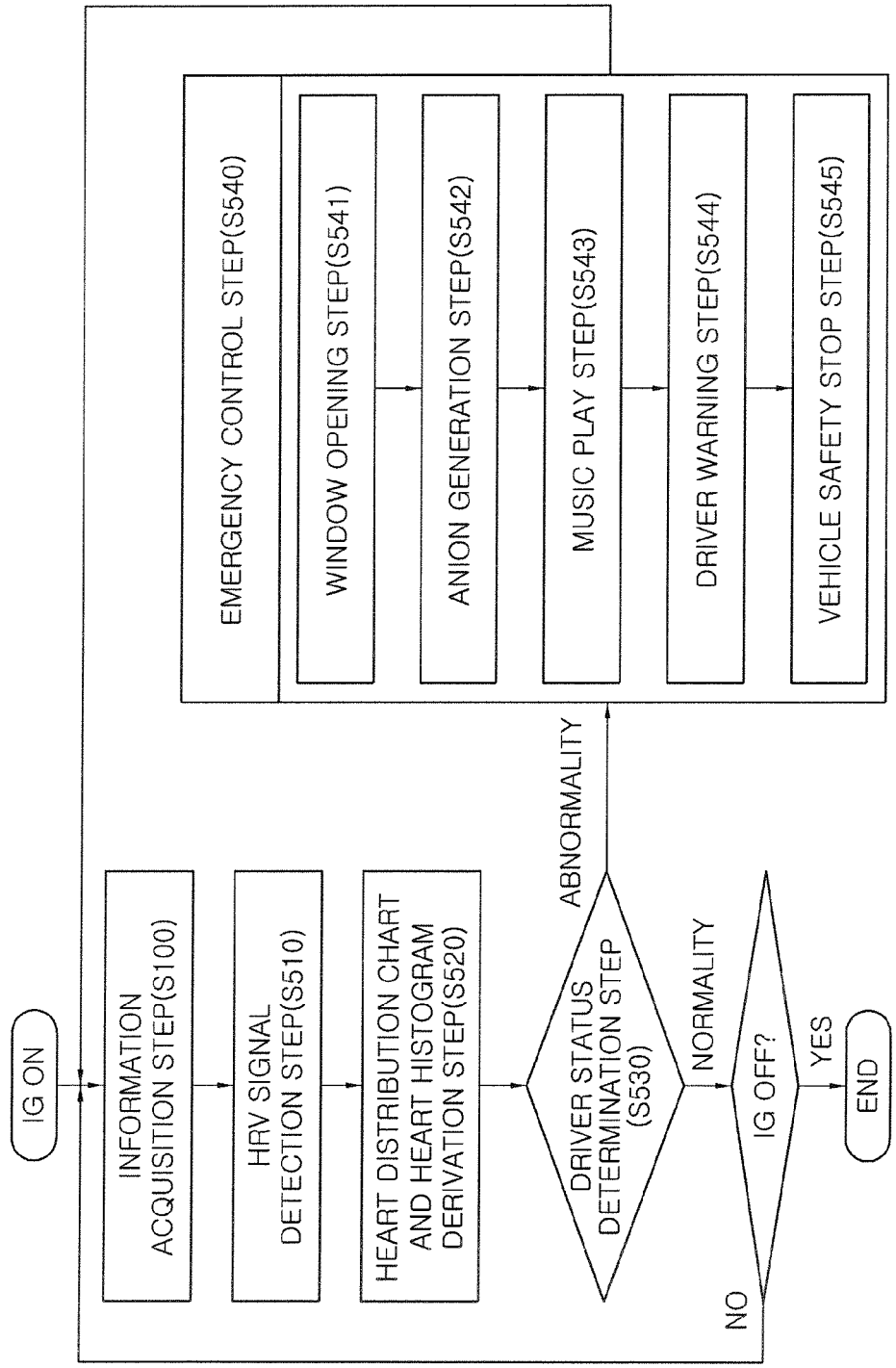
FIG. 19 is a detailed flowchart illustrating the driver status determination step utilizing the ECG according to the embodiment of the present invention.
Figure 20:
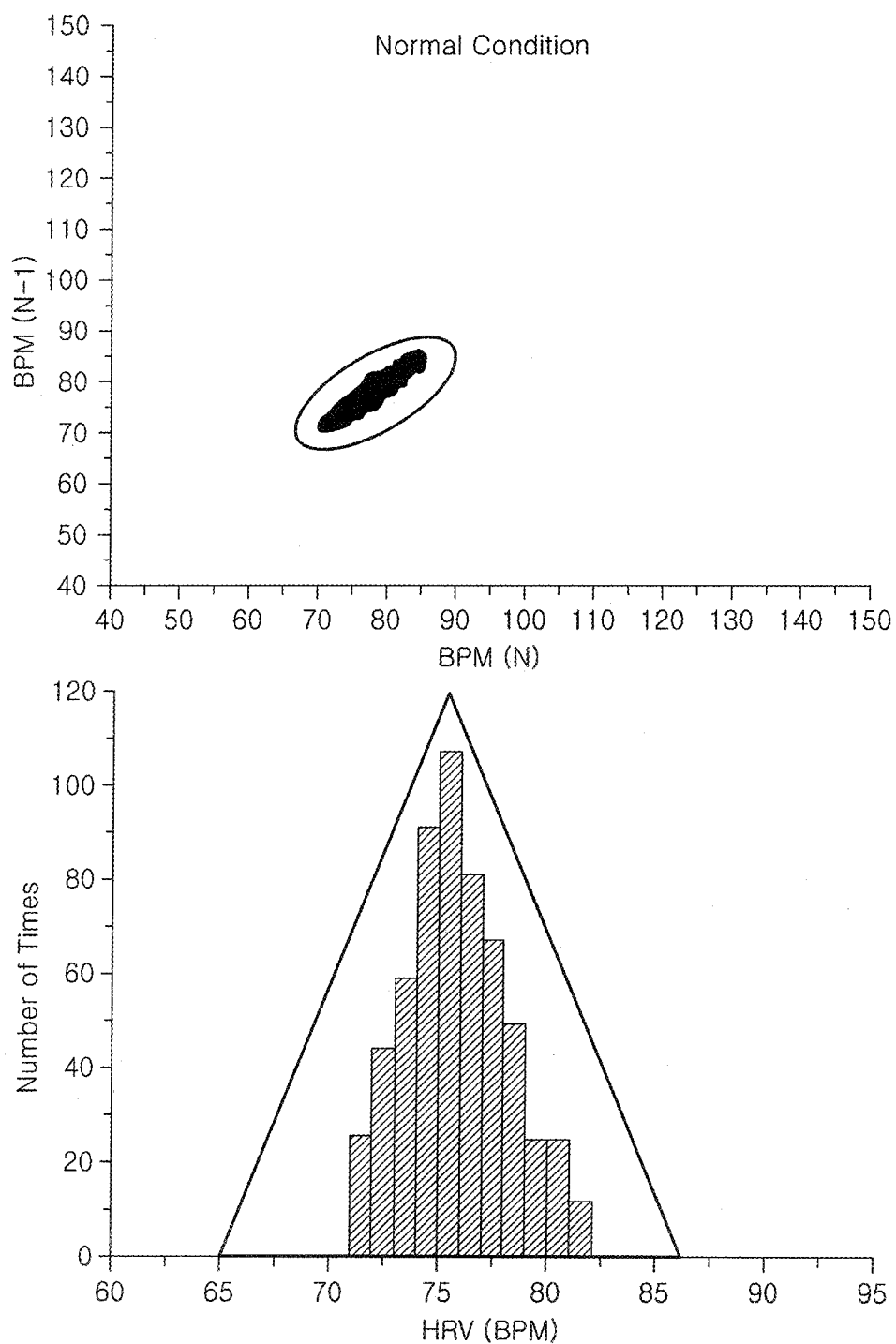
FIGS. 20 and 21 are views for explaining a method of determining a driver status from a driver's heart distribution chart and heart histogram in the method of detecting a driver status according to the embodiment of the present invention.
Figure 21:
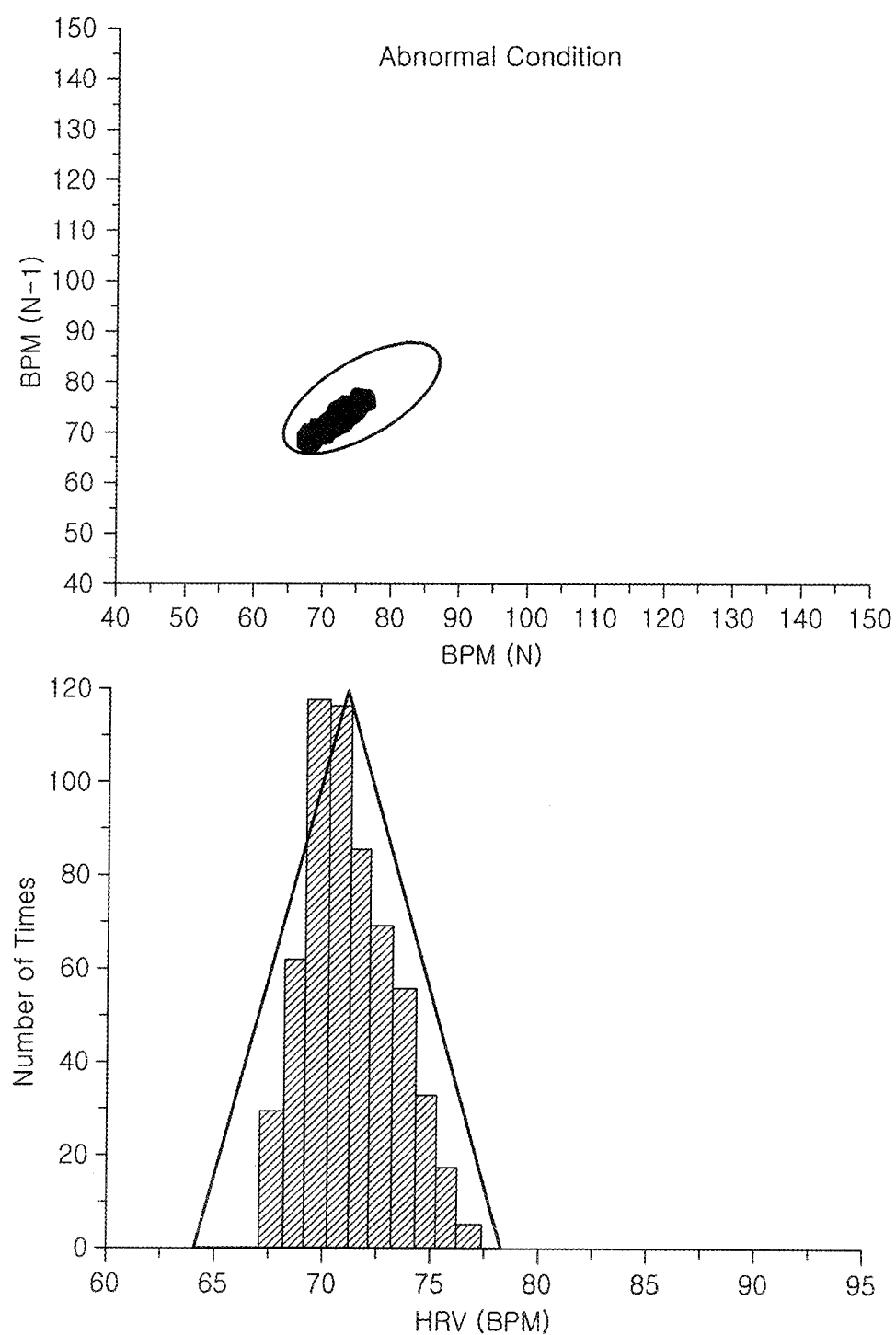

FIG. 18 is a flowchart schematically illustrating a method of detecting a driver status which includes a driver status determination step utilizing an ECG according to still another embodiment of the present invention. FIG. 19 is a detailed flowchart of FIG. 14. FIGS. 20 and 21 are views for explaining a method of determining a driver status from a driver's heart distribution chart and heart histogram. Referring to FIGS. 18 to 21, in the present invention, an HRV (Heart Rate Variability) is calculated using an ECG measurement value in order to allow a driver to directly analyze a driving load. The HRV is an index of measurement of a driver's work load, namely, the driving load, and is a method used together with an HR measurement method. Since the HRV obviously exhibits a level of difficulty to which a human body responds to stimulation, the HRV may be used as a quantified index in measuring the driving load.

As shown in FIG. 19, driver's ECG and PPG signal information is acquired through an ECG sensor and a PPG sensor as a wearable sensor in an information acquisition step S100, an HRV signal is detected from the acquired ECG and PPG signal information in an HRV signal detection step S510, a heart distribution chart and a heart histogram are derived from analysis of a time domain and frequency range of the HRV signal in a heart distribution chart and heart histogram derivation step S520, and a driver status determination step S530 determines whether a driver is in a normal condition or in an abnormal condition through the heart distribution chart and the heart histogram.

As shown in FIGS. 20 and 21, in the normal condition, it may be identified that the heart distribution chart is evenly and widely distributed within a red reference range and the heart histogram forms a large triangular shape. On the other hand, in the abnormal condition due to activation of the stress or parasympathetic nerve, it may be identified that the heart distribution chart is intensively exhibited at a low numerical value and the heart histogram forms a small triangular shape.

When the driver status determination step S530 determines that the driver is in the abnormal condition, an emergency control step S540 is separately performed without performing a calculation step S200, a comparison step S300, and a warning step S400. The emergency control step S540 may include a window opening step S541, an anion generation step S542, a music play step S543, a driver warning step S544 through an AVN or a HUD, and a vehicle safety stop step S545 through steering wheel control, transmission control, and brake control. As described above, when it is determined that the driver is in the abnormal condition in a driver status determination step utilizing an ECG S500, it is an emergency situation capable of being a deadly danger to safety of the driver. Accordingly, the emergency control step S540 is separately performed without performing the calculation step S200, the comparison step S300, and the warning step S400.

Figure 22:
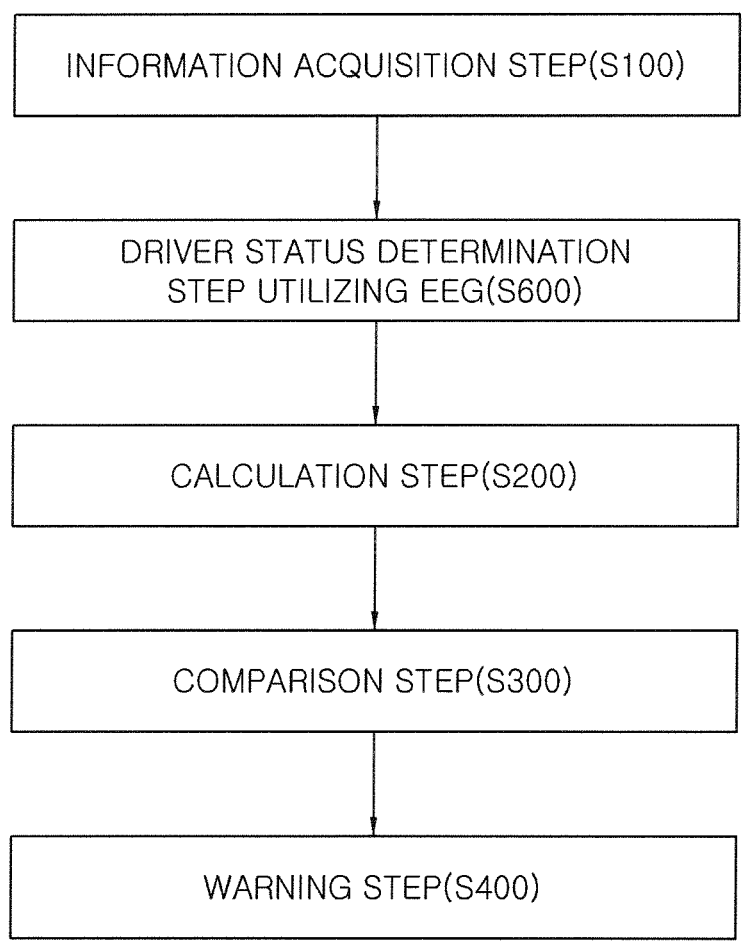
FIG. 22 is a flowchart schematically illustrating a method of detecting a driver status which includes a driver status determination step utilizing an EEG according to yet another embodiment of the present invention.
Figure 23:
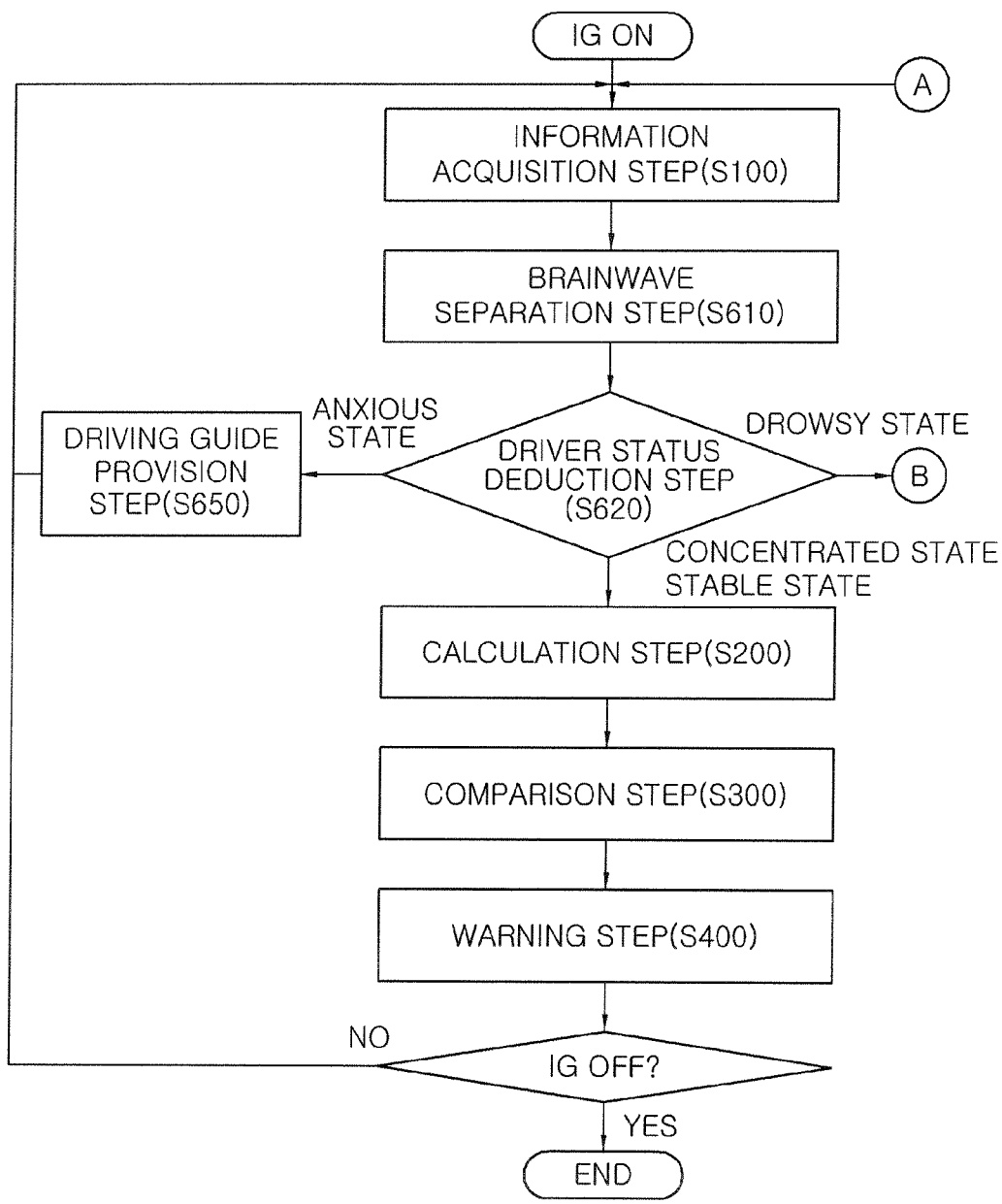
FIGS. 23 and 24 are detailed flowcharts illustrating the driver status determination step utilizing the EEG according to the embodiment of the present invention.
Figure 24:
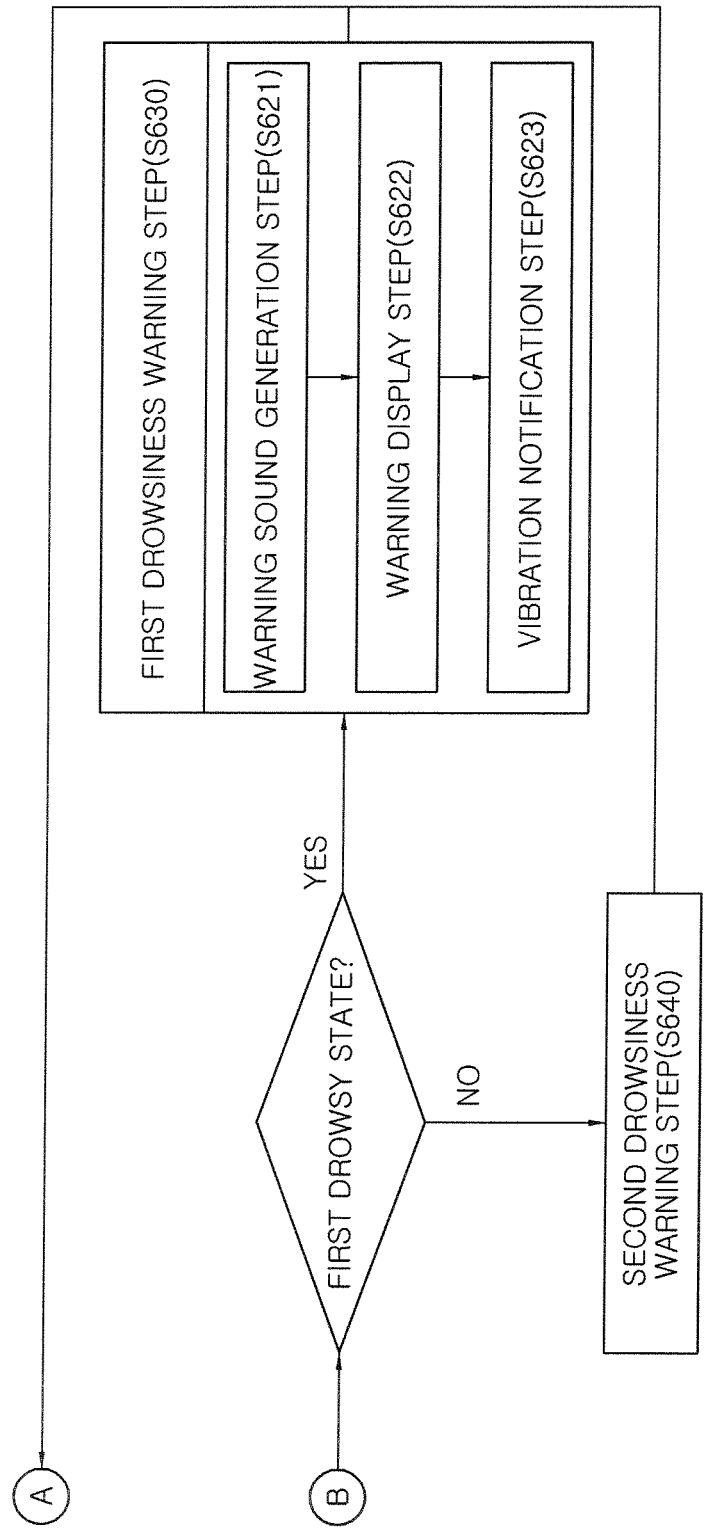
Figure 25:
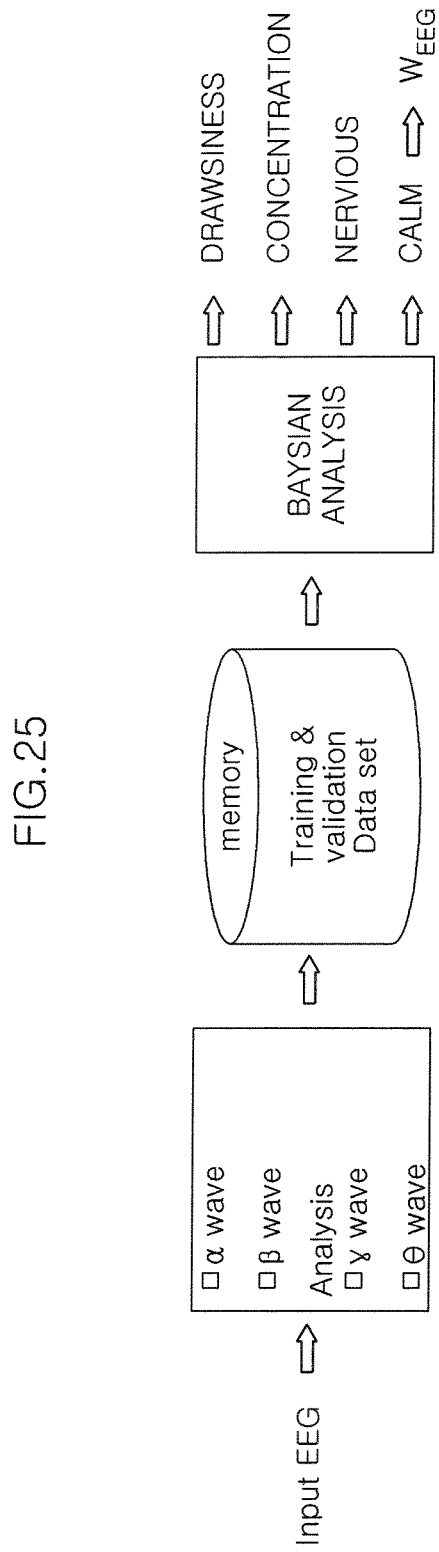
FIG. 25 is a view for schematically explaining a method of determining a driver status utilizing the EEG in the method of detecting a driver status according to the embodiment of the present invention.
Figure 27:
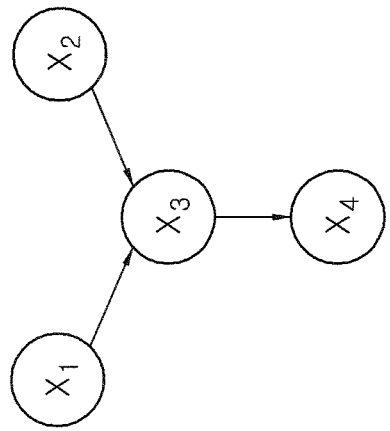
FIG. 27 is a diagram for explaining a method of finding a frequency range for each brainwave using a Bayesian network.
Figure 28:
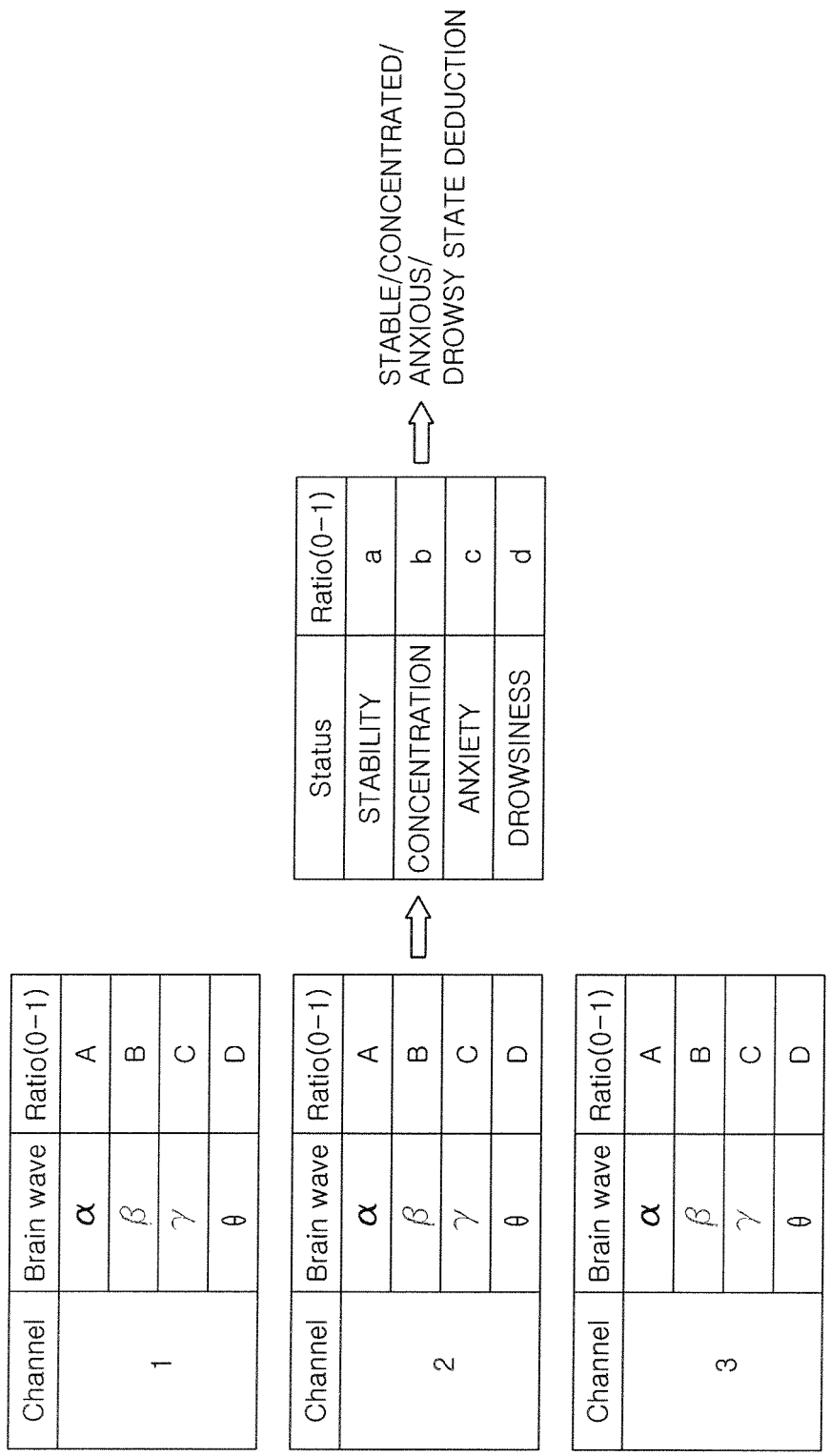
FIG. 28 is a conceptual diagram illustrating a driver status deduction step using the Bayesian network according to the embodiment of the present invention.
Figure 29:
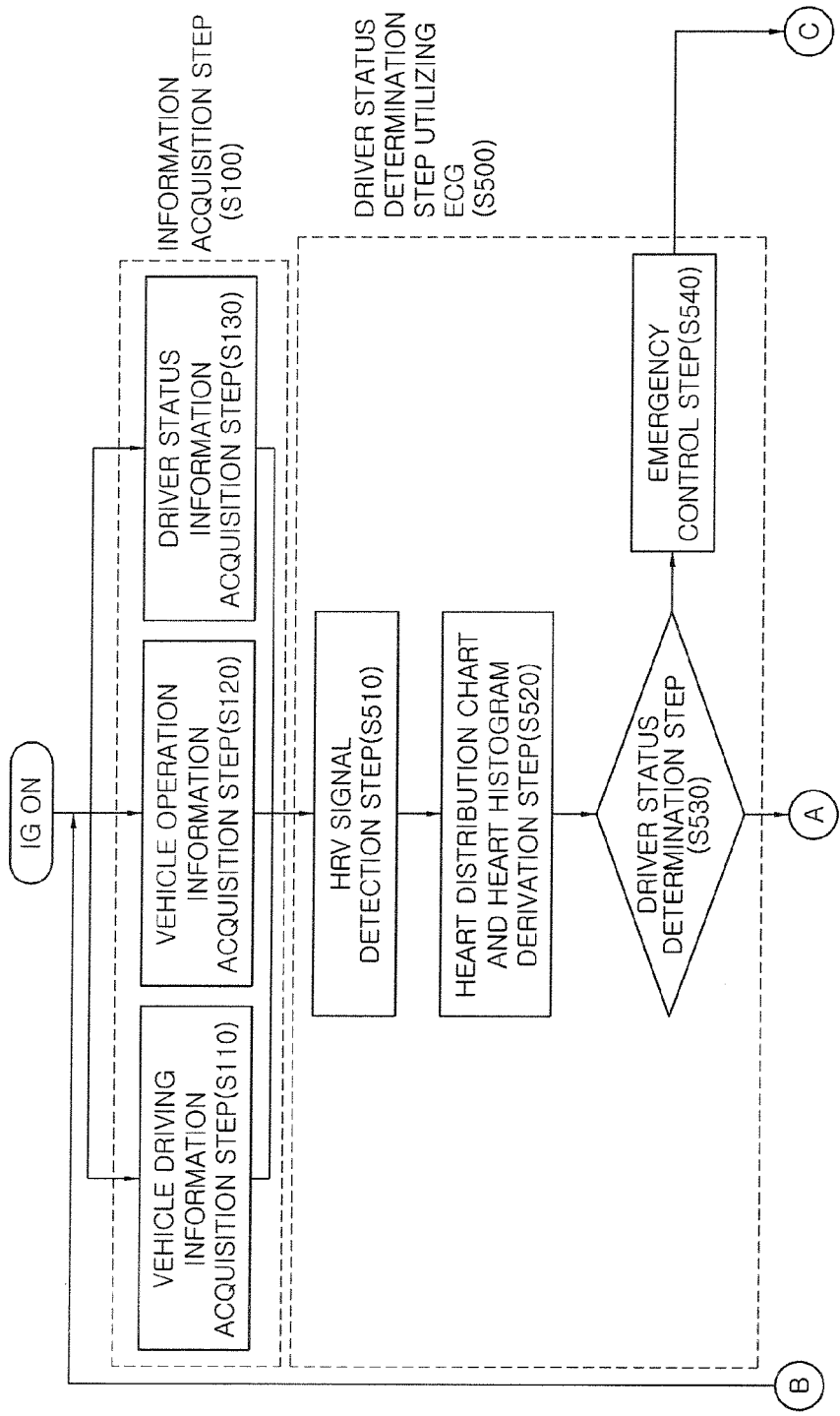
FIGS. 29 to 32 are detailed flowcharts illustrating a method of determining a driver status utilizing an ECG and an EEG according to a further embodiment of the present invention.
Figure 30:
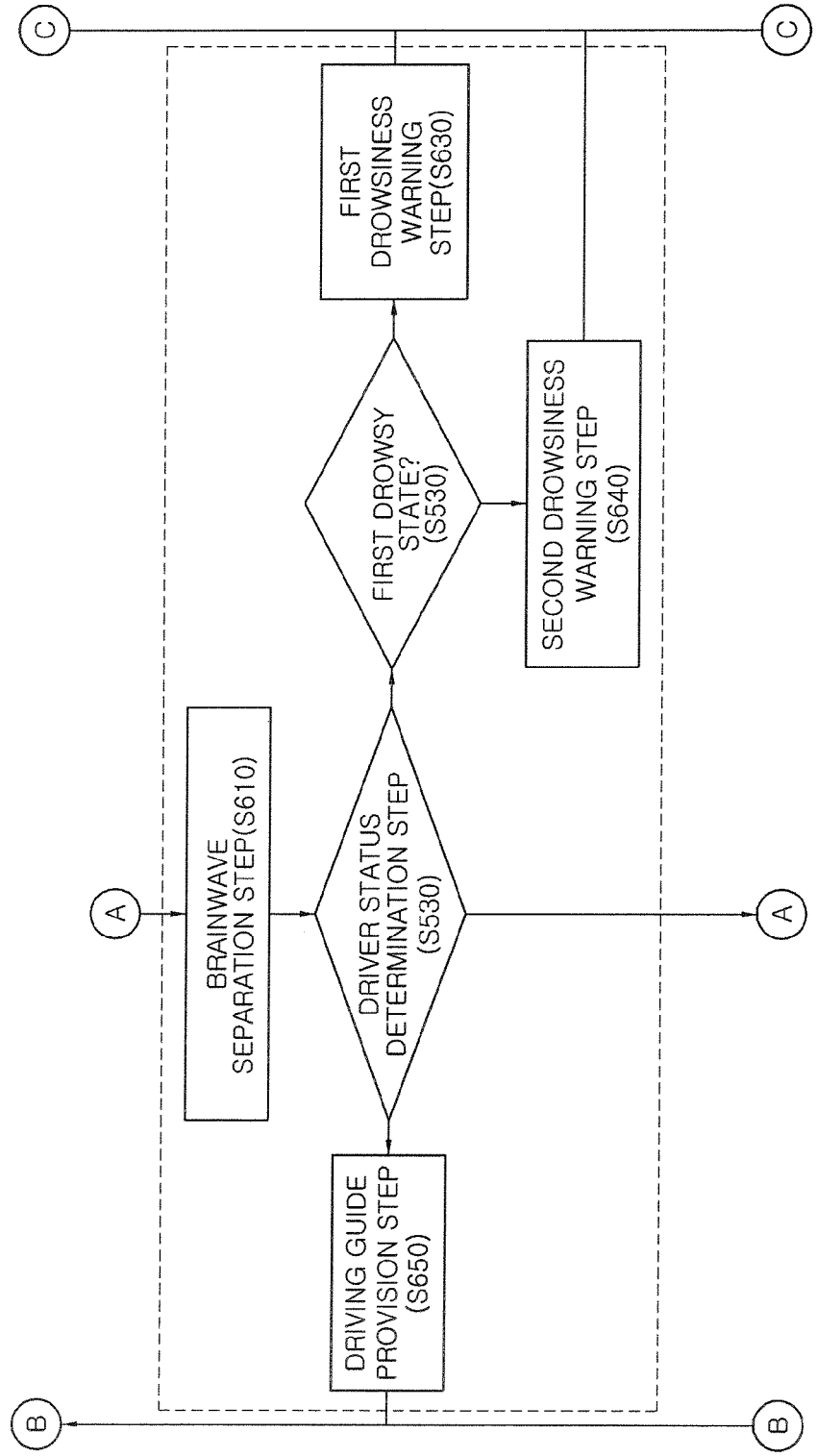
Figure 31:
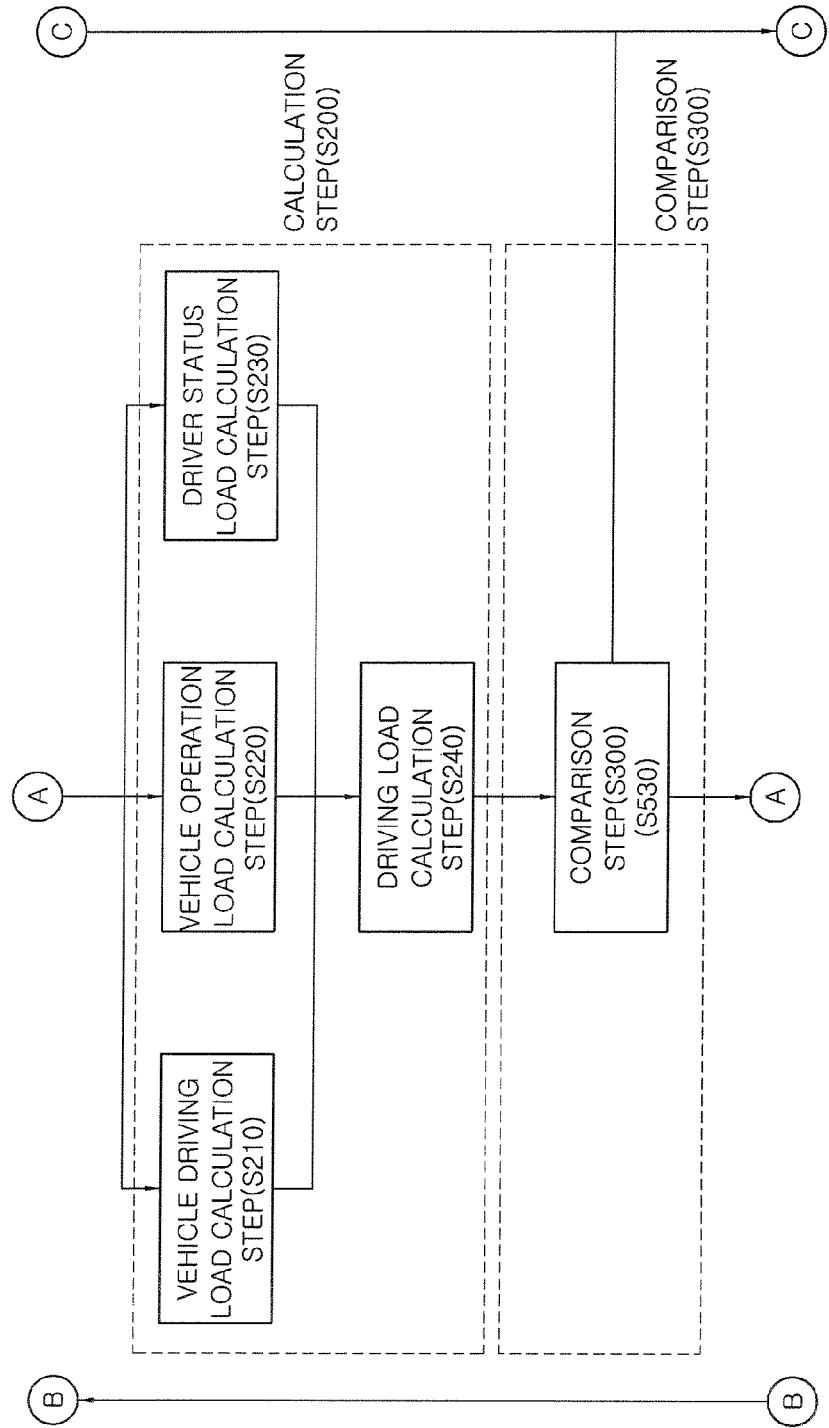
Figure 32:
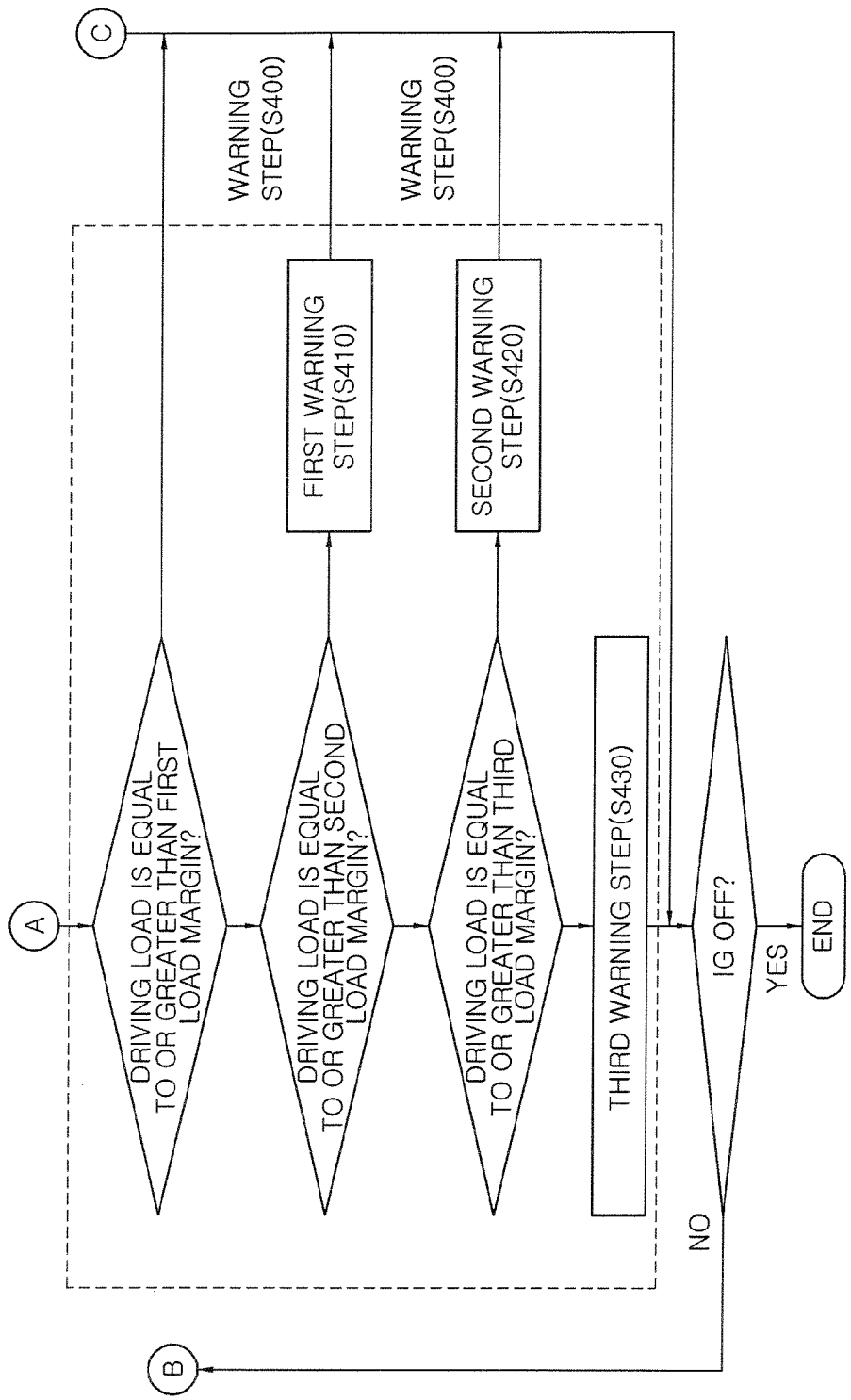

FIG. 22 is a flowchart schematically illustrating a method of detecting a driver status which includes a driver status determination step utilizing an EEG according to yet another embodiment of the present invention. FIGS. 23 and 24 are detailed flowcharts illustrating the driver status determination step utilizing the EEG. FIG. 25 is a view for schematically explaining a method of determining a driver status utilizing the EEG. FIG. 26 is a table illustrating a frequency range and characteristic of each brainwave. FIG. 27 is a diagram for explaining a method of finding a frequency range for each brainwave using a Bayesian network. FIG. 28 is a conceptual diagram illustrating a driver status deduction step using the Bayesian network. Referring to FIGS. 22 to 28, a α wave is increased in a driver's brainwave when a driver has relaxed tension or is drowsy, and a β wave is increased in the driver's brainwave when the driver feels tense and anxious. Since a brainwave activity may quantify tension and anxiety, the brainwave activity may be used as quantitative data for determination of a driving load.

As shown in FIGS. 23 and 24, a driver status is deduced at S620 by acquiring driver's brainwave information through a wearable sensor of a headset type S100, separating respective waveforms of the acquired driver's brainwave for each frequency S610, and finding a frequency range for each brainwave using a Bayesian network. That is, as shown in FIGS. 25 to 28, the driver status may be finally deduced using a method of determining a comparison between the drive status and existing data by indicating an uncertain situation as a probability value through the Bayesian network and simplifying a complicated deduction process as a relation between quantitative nodes. The existing data may be stored in the memory portion 50.

The driver status deduction step S620 determines whether or not the driver is in a first drowsy state when the driver is deduced to be in a drowsy state. When it is determined that the driver is in the first drowsy state, a first drowsiness warning step S630 is performed. The first drowsiness warning step S630 includes steps, such as a music play or warning sound generation step S621 through a speaker, a warning display step S622 through an AVN or a HUD, and a vibration notification step S623 through vibration of a steering wheel or a seat, which are capable of awakening the driver from the drowsy state. In order to identify whether or not the driver is awakened from the drowsy state after the first drowsiness warning step S630, the information acquisition step S100, the brainwave separation step S610, and the driver status deduction step S620 are performed again. When the driver status deduction step S620 deduces that the driver is in a second drowsy state despite execution of the first drowsiness warning step S630, the process performs a second drowsiness warning step S640 of safely stopping the vehicle through steering wheel control, transmission control, and brake control. That is, when the driver is restored to the awakened state despite the first and second drowsiness warnings, the vehicle is autonomously stopped in a safe region against control of the driver. Consequently, it may possible to protect the drowsy driver. As described above, when it is deduced that the driver is in the drowsy state in a driver status determination step utilizing an EEG S600, it is an emergency situation capable of being a deadly danger to safety of the driver. Accordingly, the first and second drowsiness warning steps S630 and S640 are separately performed without performing a calculation step S200, a comparison step S300, and a warning step S400.

When the driver status deduction step S620 deduces that the driver is in an anxious state, a system determines an operation condition algorithm for vehicle driving such that errors are not present in the algorithm, so as to provide the driver with a driving guide through the AVN or the HUD S650. As described above, when it is deduced that the driver is in the anxious state in the driver status determination step utilizing an EEG S600, it is an emergency situation capable of being a deadly danger to safety of the driver. Accordingly, the driving guide provision step S650 is separately performed without performing the calculation step S200, the comparison step S300, and the warning step S400.

When it is deduced that the driver is in a concentrated or stable state in the driver status deduction step S620, the calculation step S200 including calculation of a brainwave load $W_{EEG}$ is performed. The brainwave load $W_{EEG}$ is calculated through a signal ratio in the concentrated or stable state, as in the following equation:

$$W_{EEG} = \frac{\alpha \text{ wave}(8 \sim 12.99 \text{ Hz})}{\beta \text{ wave}(13 \sim 29.99 \text{ Hz})}.$$

When a α wave value becomes a maximum value (12.99 Hz) by dividing a mean frequency value of the α wave and β wave extracted for a unit time, the greatest value of the brainwave load $W_{EEG}$ approximates 1. Accordingly, the brainwave load $W_{EEG}$ is maximized. In addition, the contraposition is established. A value, which multiplies the calculated value of the brainwave load $W_{EEG}$ by a brainwave load correction value φ calculated by an experiment, is summed in the calculation step S200, as in the following equation:

$$W_{total} = W_D + W_M + W_i + \phi + W_{EED}$$

$W_{total}$=driving load
$W_D$=vehicle driving load
$W_M$=vehicle operation load
$W_i$=driver status load
$W_{EED}$=brainwave load
φ=brainwave load correction value.

FIGS. 29 to 32 are detailed flowcharts illustrating a method of determining a driver status utilizing an ECG and an EEG according to a further embodiment of the present invention. As shown in FIG. 23, a method of detecting a driver status according to an exemplary embodiment of the present invention may be performed in order of an information acquisition step S100, a driver status determination step utilizing an ECG S500, a driver status determination step utilizing an EEG S600, a calculation step S200, a comparison step S300, and a warning step S400. A method of detecting a driver status according to another exemplary embodiment of the present invention may also be performed in reversed order of a driver status determination step utilizing an ECG S500 and a driver status determination step utilizing an EEG S600. That is, the method may be performed in order of an information acquisition step S100, a driver status determination step utilizing an EEG S600, a driver status determination step utilizing an ECG S500, a calculation step S200, a comparison step S300, and a warning step S400.

As is apparent from the above description, an apparatus and method for detecting a driver status according to the exemplary embodiments of the present invention may grasp a driver's mental and physical condition relevant to vehicle driving or operations by a driver to determine whether or not the driver drives a vehicle with safety and induce the driver to drive the vehicle with safety in various ways, such as warning signs, generation of warning sound, vibration notification, and forced control of the vehicle, when the driver is determined not to be in a safe driving state so as to protect the driver. Particularly, since the apparatus and method for detecting a driver status may grasp serious issues, such as a driver's seizure or abnormal emotion, labored respiration, neglect of observation, and poor driving, in regard to the driver's mental and physical condition, which are difficult to be determined in the related art, it may be very useful.

While the present invention has been described with respect to the specific embodiments, it will be apparent to those skilled in the art that various changes and modifications may be made without departing from the spirit and scope of the invention as defined in the following claims.

What is claimed is:
1. An apparatus for controlling a vehicle based on detecting a driver status, the apparatus comprising:
an information acquisition unit configured to acquire driver status information that comprises signals indicative of heart conditions of a driver while the driver is driving the vehicle; and
at least one processor configured to perform at least one predetermined processing of the signals and further configured to determine whether the driver is in an abnormal condition at least based on results of the at least one predetermined processing of the signals;
wherein the at least one processor is further configured to perform an emergency control routine for a forced stop of the vehicle via a steering control, a transmission control and a brake control against the driver's control of the vehicle when it is determined that the driver is in an abnormal condition while driving,
wherein the at least one processor is further configured to determine a driver status utilizing the driver's brainwave information from an EEG sensor,
wherein determining the driver status comprises computing a brainwave load using the following equation:

$$W_{EED} = \varphi \times \frac{\alpha \text{ wave}}{\beta \text{ wave}}$$

wherein $W_{EED}$=brainwave load,
φ=preset brainwave load weighting,
α wave=mean frequency of α wave extracted for a unit time, and
β wave=mean frequency of β wave extracted for a unit time.

2. The apparatus of claim 1, further comprising:
a calculation unit configured to calculate a driving load by converting a factor obstructing safe driving into a numerical value, based on the information acquired by the information acquisition unit;
a comparison unit configured to compare between the driving load calculated by the calculation unit and a preset load margin;
a warning unit configured to provide a warning to the driver when the comparison unit determines that the calculated driving load exceeds the preset load margin; and
the information acquisition unit further comprising a vehicle driving information acquisition portion, a vehicle operation information acquisition portion, and a driver status information acquisition portion,
wherein the at least one processor further configured to perform the emergency control routine for a forced stop of the vehicle without the warning from the warning unit.

3. The apparatus of claim 2, wherein the vehicle driving information acquisition portion comprises one or more of an accelerator pedal operation sensor, a brake pedal operation sensor, a steering wheel operation sensor, a multifunctional switch operation sensor, a clutch pedal operation sensor, and a transmission operation sensor, in order to acquire information generated when the driver drives a vehicle.

4. The apparatus of claim 2, wherein the vehicle operation information acquisition portion comprises one or more of an air conditioning device switch operation sensor and an AVN (audio/video/navigation) switch operation sensor, in order to acquire information generated when the driver operates a vehicle.

5. The apparatus of claim 2, wherein the driver status information acquisition portion comprises one or more of a microphone, a driver observation camera, an ECG (electrocardiogram) sensor, an EEG (electroencephalogram) sensor, and a PPG (photoplethysmography) sensor, in order to acquire information according to a driver status during driving of a vehicle.

6. The apparatus of claim 2, wherein the warning unit comprises one or more of a warning sound output device, a driving load display device, and a vehicle control device.

7. The apparatus of claim 1, wherein the signals of heart condition are from at least one of an ECG sensor and a PPG sensor.

8. A method of controlling a vehicle based on detecting a driver status, comprising:
acquiring, using a sensor, driver's status information while the vehicle is being driven by a driver, the driver status information comprising signals indicative of heart conditions of the driver while the driver is driving the vehicle;
performing, using at least one processor, at least one predetermined processing of the signals and determining whether the driver is in an abnormal condition at least based on results of the at least one predetermined processing of the signals;
when it is determined that the driver is in an abnormal condition while driving, performing, using the at least one processor, an emergency control routine for a forced stop of the vehicle via a steering control, a transmission control and a brake control against the driver's control of the vehicle; and
determining, using the at least one processor, a driver status utilizing the driver's brainwave information from an EEG sensor, wherein determining the driver status comprises computing a brainwave load using the following equation:

$$W_{EED} = \varphi \times \frac{\alpha \text{ wave}}{\beta \text{ wave}}$$

wherein $W_{EED}$=brainwave load,
$\varphi$=preset brainwave load weighting,
$\alpha$ wave=mean frequency of $\alpha$ wave extracted for a unit time, and
$\beta$ wave=mean frequency of $\beta$ wave extracted for a unit time.

9. The method of claim 8, further comprising:
calculating a driving load by converting a factor obstructing safe driving into a numerical value, based on the acquired information;
comparing the calculated driving load with a preset load margin; and
warning the driver when the driving load of the driver exceeds the preset load margin,
wherein acquiring further comprises acquiring vehicle driving information, and acquiring vehicle operation information,
wherein, when it is determined that the driver is in an abnormal condition, the emergency control routine for a forced stop of the vehicle is performed before calculating, comparing and warning.

10. The method of claim 9, wherein the driving information comprises one or more of accelerator pedal operation information, brake pedal operation information, steering wheel operation information, and multifunctional switch operation information which are generated when the driver drives a vehicle.

11. The method of claim 9, wherein the vehicle operation information comprises one or more of AVN operation information and air conditioning device operation information which are generated when the driver operates a vehicle.

12. The method of claim 9, wherein the driver's status information further comprises one or more of driver's voice information, driver's forward observation information, driver's eye-closed information, and driver's brainwave information which are indicative of a driver status during driving of a vehicle.

13. The method of claim 9, wherein the calculating a driving load comprises calculating a vehicle driving load, calculating a vehicle operation load, calculating a driver status load, and calculating a driving load by summing the respective calculated loads.

14. The method of claim 9, wherein when the driving load is equal to or greater than a first load margin and less than a second load margin, the warning the driver performs a first warning process comprising one or more of generating a warning sound through a speaker, displaying a warning through an AVN or a HUD, and notifying of vibration through vibration of a steering wheel or a seat.

15. The method of claim 9, wherein when the driving load is equal to or greater than a second load margin and less than a third load margin, the warning the driver performs a second warning process of holding a function of an AVN.

16. The method of claim 9, wherein when the driving load is equal to or greater than a third load margin, the warning the driver performs a third warning process of forcibly stopping a vehicle.

17. The method of claim 8, wherein performing driver status determination comprises:

performing brainwave separation of separating respective waveforms from the driver's brainwave information for each frequency, deducing a driver's status through a Bayesian network, based on the respective waveforms separated for each frequency in the performing brainwave separation, performing a first drowsiness warning process, when the driver is deduced to be in a first drowsy state in the deducing a driver's status, performing a second drowsiness warning process of safely stopping the vehicle, when the driver is deduced to be in a drowsy state other than the first drowsy state in the deducing a driver's status, and providing a driving guide through an AVN or a HUD, when the driver is deduced to be in an anxious state in the deducing a driver's status, wherein the performing a first drowsiness warning process includes one or more of playing music or generating a warning sound through a speaker, displaying a warning through the AVN or the HUD, and notifying of vibration through vibration of a steering wheel or a seat.

18. The method of claim 8, wherein the signals of heart condition are from at least one of an ECG sensor and a PPG sensor.

* * * * *